United States Patent

Lupo et al.

[11] Patent Number: 5,840,217
[45] Date of Patent: Nov. 24, 1998

[54] SPIRO COMPOUNDS AND THEIR USE AS ELECTROLUMINESCENCE MATERIALS

[75] Inventors: Donald Lupo, Frankfurt; Josef Salbeck, Kelkheim; Hermann Schenk, Hofheim; Thomas Stehlin, Kriftel; Roland Stern, Wiesbaden; Arno Wolf, Mainz, all of Germany

[73] Assignee: Hoechst Aktiengesellschaft, Frankfurt, Germany

[21] Appl. No.: 417,390

[22] Filed: Apr. 5, 1995

[30] Foreign Application Priority Data

Apr. 7, 1994 [DE] Germany .................. 44 11 969.0
Nov. 25, 1994 [DE] Germany .................. 44 42 063.3
Dec. 27, 1994 [DE] Germany .................. 44 46 818.0

[51] Int. Cl.$^6$ .............. G02F 1/00; H01B 1/00; H01J 1/62
[52] U.S. Cl. .............. 252/583; 252/500; 585/27; 313/504; 544/230; 546/15; 548/136; 548/143; 548/147; 548/216; 548/262.2; 548/267.2; 548/300.7; 548/407
[58] Field of Search ................... 252/700, 500, 252/583; 585/27; 313/504; 544/230; 546/15; 548/136, 143, 147, 216, 262.2, 267.2, 300.7, 407; 564/426

[56] References Cited

U.S. PATENT DOCUMENTS

| | | | |
|---|---|---|---|
| 3,906,283 | 9/1975 | Bard et al. .................. | 252/700 |
| 5,026,894 | 6/1991 | Tour et al. . | |
| 5,151,629 | 9/1992 | Van Slyke . | |
| 5,504,183 | 4/1996 | Shi et al. .................. | 252/500 |
| 5,543,079 | 8/1996 | Ohnishi et al. .................. | 252/800 |

FOREIGN PATENT DOCUMENTS

| | | |
|---|---|---|
| 0120673 | 10/1984 | European Pat. Off. . |
| 0502202 | 9/1992 | European Pat. Off. . |
| 0510541 | 10/1992 | European Pat. Off. . |
| 43 31 401 | 3/1995 | Germany . |

OTHER PUBLICATIONS

J. Am. Chem. Soc. (1990), 112, pp. 5662–5663 XP002030896.
Chem. Abstract XP 002030897, by Tour et al., pp. 408–409, (1990).
J.S.D.C. (1978), XP002030898, by Sutcliffe et al. pp. 306–308.
Liebigs Ann. Chem. (1981), XP002030899, by Liphardt et al., pp. 1118–1138.
Helvetica Chimica Acta, vol. 52, Fasc. 5 (1969), XP002030900, by Haas et al.
Helvetica Chimica Acta, vol. 62, Fasc. 7 (1979), XP002030901, by Prelog et al.
Tour, J. et al., "Approaches to Orthogonally Fused Conducting Polymers for Molecular Electronics" J. Am. Chem. Soc. 1990, 112, 5662–5663.
Tour, J. et al., "Spiro–Fused Conducting Polymers for Molecular Electronics" J. Am. Chem. Soc. 1990, 408–409.

*Primary Examiner*—Philip Tucker
*Attorney, Agent, or Firm*—Frommer Lawrence & Haug LLP

[57] ABSTRACT

Use of spiro compounds of the formula (I)

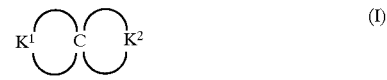

where $K^1$ and $K^2$ are, independently of one another, conjugated systems, in electroluminescence devices.

Preferred compounds of the formula (I) are 9,9'-spirobifluorene derivatives of the formula (II)

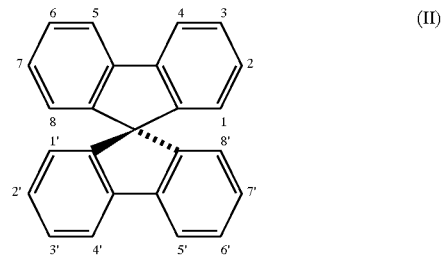

where the benzo groups can be substituted independently of one another.

Compounds of the formula (I) have a good solubility in customary organic solvents, improved film-forming properties and a significantly reduced tendency to crystallize. The production of electroluminescence devices is thereby made easier and their service life is increased.

12 Claims, No Drawings

SPIRO COMPOUNDS AND THEIR USE AS ELECTROLUMINESCENCE MATERIALS

There is a great industrial need for large-area solid state light sources for a series of applications, predominantly in the fields of display elements, VDU technology and lighting engineering. The demands made of these light sources can at present not be met with complete satisfaction by any of the existing technologies.

As an alternative to conventional display elements, such as incandescent lamps, gas-discharge lamps and liquid crystal display elements which do not produce light themselves, knowledge has existed for some time of electroluminescence (EL) materials and devices, such as light-emitting diodes (LEDs).

Electroluminescence materials are substances which are capable of radiating light on application of an electric field. The physical model for describing this effect is based on the radiating recombination of electrons and electron gaps (holes). In the case of light-emitting diodes, the charge carriers are injected into the electroluminescence material via the cathode or anode. Electroluminescence devices comprise a luminescent material as light-emitting layer.

Electroluminescence materials and devices are generally described, for example, in Ullmann's Encyclopedia of Industrial Chemistry, Vol. A9, 5th Ed. VCH Verlag 1987 and the literature cited therein.

Apart from inorganic materials, such as ZnS/Mn or GaBs, organic compounds have also become known as EL materials.

A description of EL devices containing low-molecular-weight organic EL materials is given, for example, in U.S. Pat. No. 4,539,507.

Disadvantages of these low-molecular-weight organic materials are, for example, the unsatisfactory film-forming properties and a pronounced tendency to crystallize.

Recently, polymers have also been described as EL materials (see, for example, WO-A 90/13148). However, the light yield (quantum efficiency) of these materials is considerably lower than for the low-molecular-weight compounds.

It was desirable to find EL materials which give good light yields and at the same time can be processed into thin homogeneous films which have a low tendency to crystallize.

It has now surprisingly been found that spiro compounds, in particular derivatives of 9,9'-spirobifluorene, are very suitable as EL materials.

Individual compounds of this type have been described as linking elements for polymeric, organic semiconductors and have been proposed as materials for molecular electronics, for example in U.S. Pat. No. 5,026,894, J. M. Tour et al., J. Am. Chem. Soc. 112 (1990) 5662 and J. M. Tour et al., Polym. Prepr. (1990) 408. However, nothing is said about a possible use as EL materials.

The invention accordingly provides for the use of spiro compounds of the formula (I),

(I)

where
K$^1$ and K$^2$ are, independently of one another, conjugated systems, in electroluminescence devices.

Compounds of the formula (I) are readily soluble in customary organic solvents, have improved film-forming properties and have a significantly reduced tendency to crystallize. This makes the production of electroluminescence devices easier and increases their service life. The emission properties of the compounds used according to the invention can be set over the entire range of the visible spectrum by selection of suitable substituents. Furthermore, the covalently bonded arrangement of the two parts of the spiro compound allows construction of the molecule in such a way that particular properties can be independently set in the two halves of the molecule. Thus, one half can possess, for example, charge-transport or charge-injection properties, while the other half possesses light-emitting properties. The spatial proximity of the two halves, which is fixed by the covalent linkage, is in this context favorable for energy transfer (see, for example, B. Liphardt, W. Lüttke, Liebigs Ann. Chem. (1981) 1118).

Preferred compounds of the formula (I) are 9,9'-spirobifluorene derivatives of the formula (II),

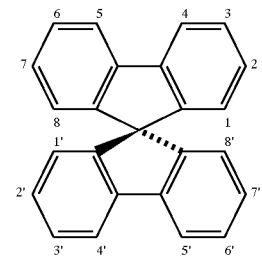

(II)

where the benzo groups can be substituted and/or fused independently of one another.

Particular preference is given to spirobifluorene derivatives of the formula (III)

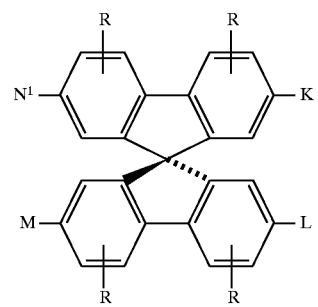

(III)

where the symbols and indices have the following meanings:

K, L, M, N' are identical or different and are

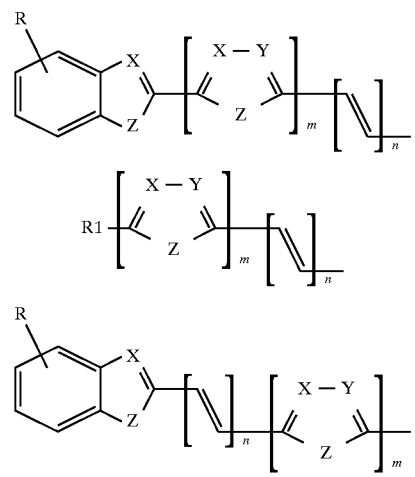

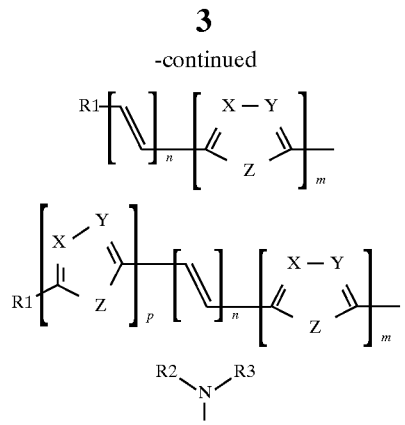

R can be identical or different on each appearance and have the same meanings as K, L, M, N or is H, a linear or branched alkyl, alkoxy or ester group having from 1 to 22, preferably from 1 to 15, particularly preferably from 1 to 12, carbon atoms, —CN, —NO$_2$, —NR$^2$R$^3{}_1$, —Ar or —O—Ar;

Ar is phenyl, biphenyl, 1-naphthyl, 2-naphthyl, 2-thienyl, 2-furyl, with each of these groups being able to bear one or two radicals R, m, n, p are 0, 1, 2 or 3;

X, Y are identical or different and are CR or nitrogen;

Z is —O—, —S—, —NR$^1$—; —CR$^1$R$^4$—, —CH=CH—, —CH=N—;

R$^1$, R$^4$ can be identical or different and have the same meanings as R;

R$^2$, R$^3$ are identical or different and are H, a linear or branched alkyl group having from 1 to 22 carbon atoms, —Ar, 3-methylphenyl.

Preferred compounds of the formula (III) are those of the formulae (IIIa)–(IIIg)

IIIa) K=L=M=N and is selected from the group consisting of:

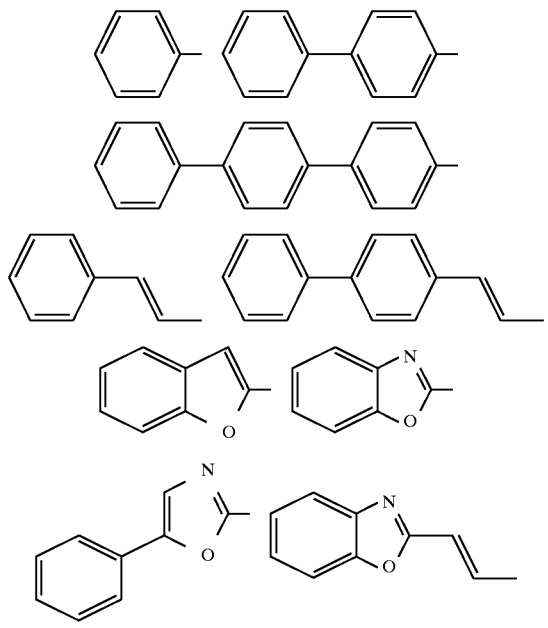

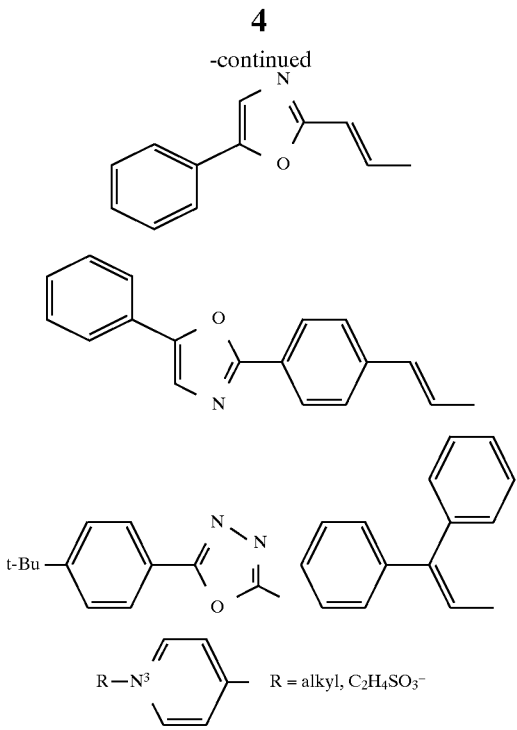

R=C$_1$–C$_{22}$-alkyl, C$_2$H$_4$SO$_3{}^-$

IIIb) K=M=H and N=L and is selected from the group consisting of:

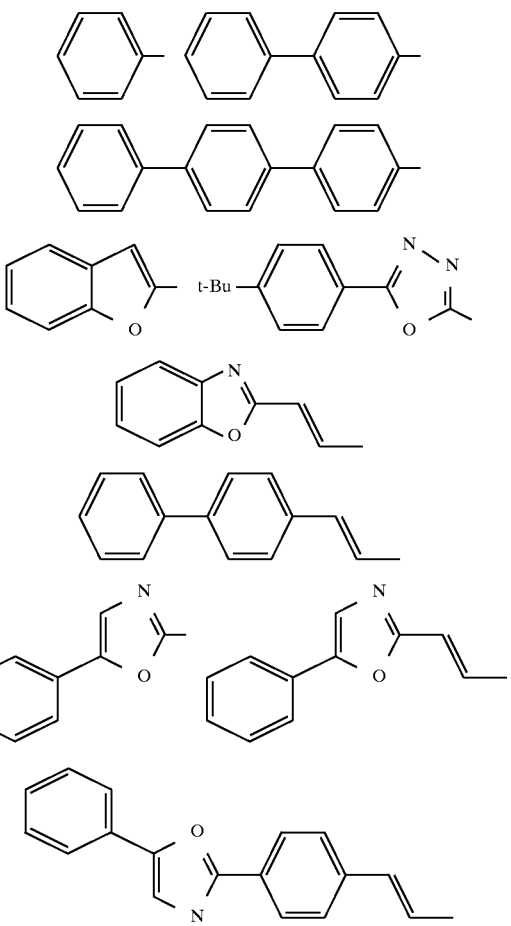

-continued
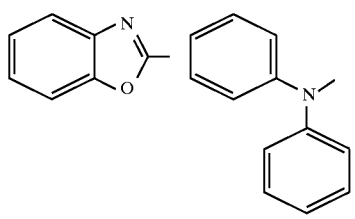
IIIc) K=M and is selected from the group consisting of:
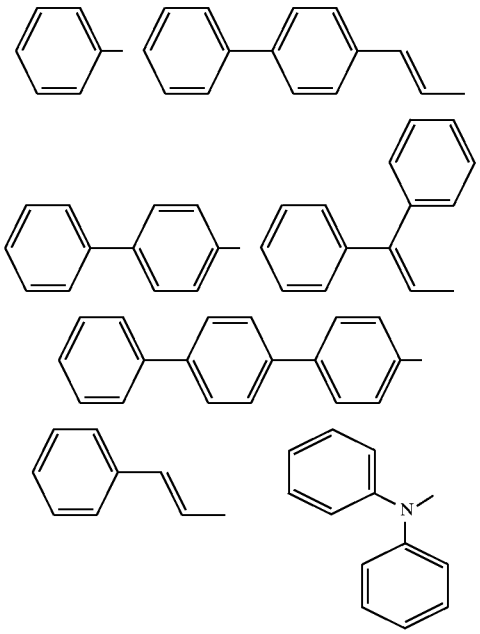
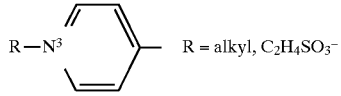   R = alkyl, $C_2H_4SO_3^-$
and N=L and is selected from the group consisting of:
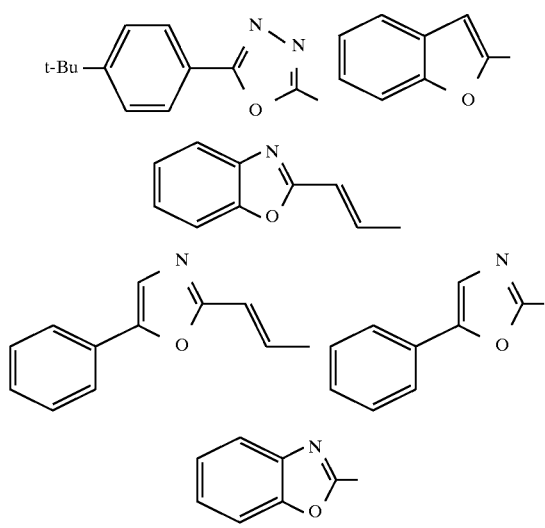
-continued
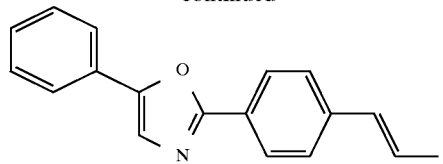
IIId) K=M and is selected from the group consisting of:
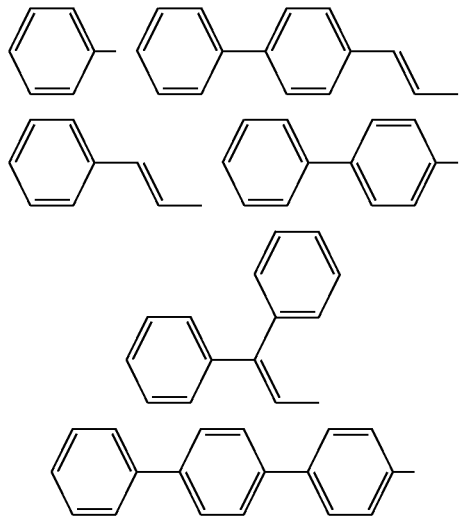
and N=L and is selected from the group consisting of:
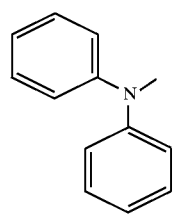
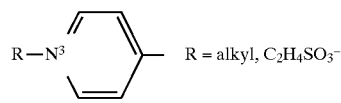   R = alkyl, $C_2H_4SO_3^-$
IIIe) K=L=H and M=N and is selected from the group consisting of:
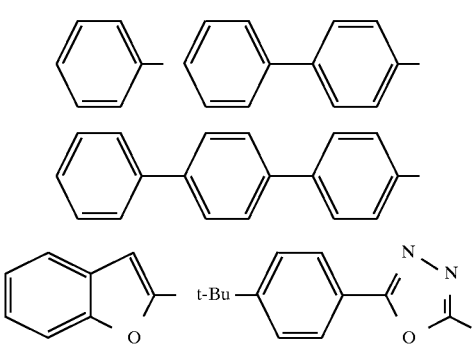

-continued
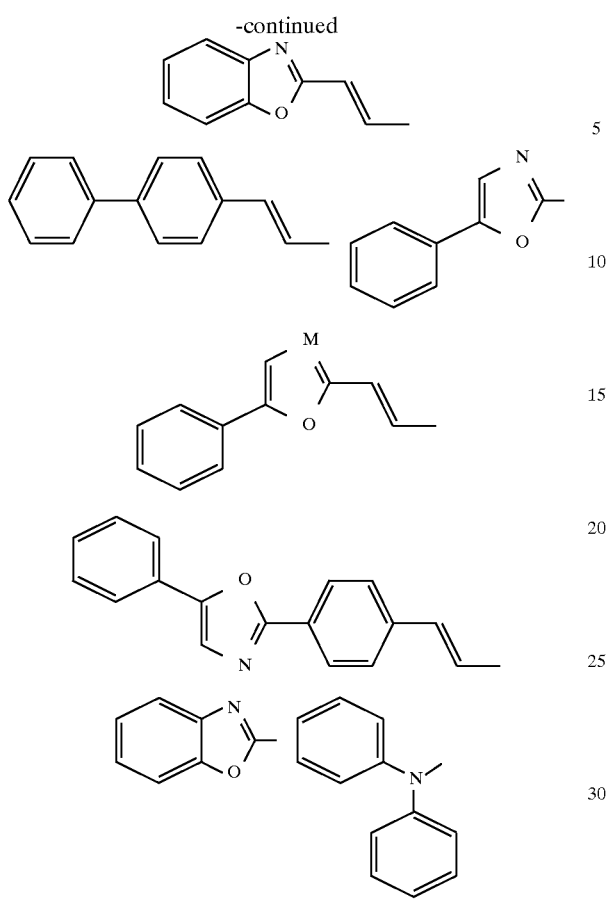
IIIf) K=L and is selected from the group consisting of:
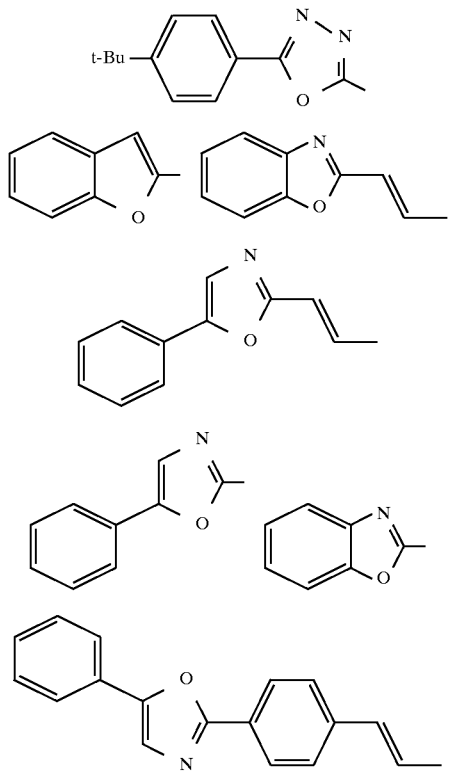
and M=N and is selected from the group consisting of:
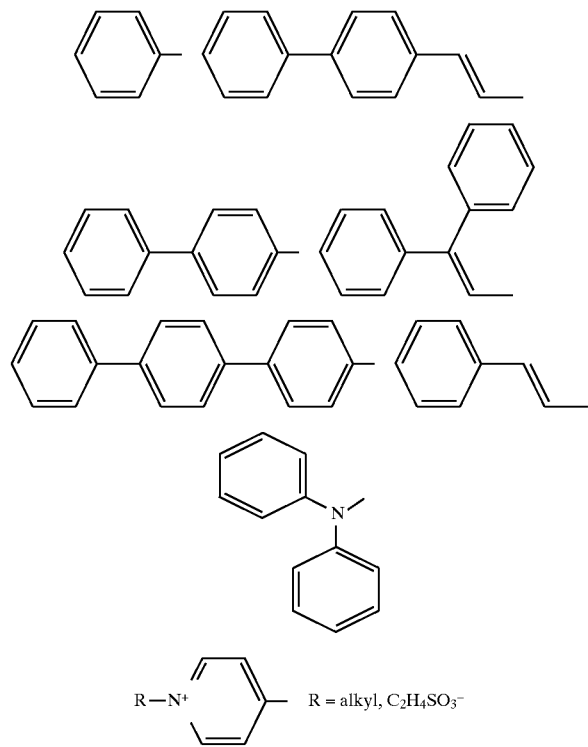
IIIg) K=L and is selected from the group consisting of:
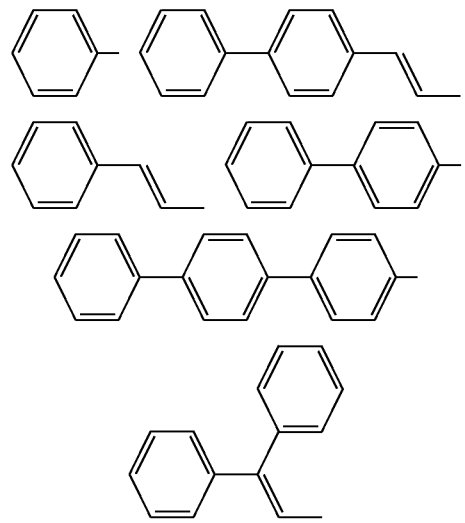
and M=N and is selected from the group consisting of:
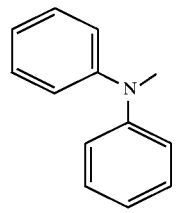

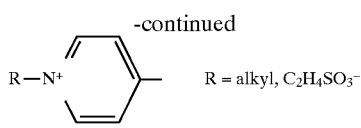

R = alkyl, C₂H₄SO₃⁻

Particularly preferred compounds of the formula (III) are those of the formulae (IIIaa) to (IIIdb):

(IIIaa) K=L=M=N and is selected from the group consisting of:

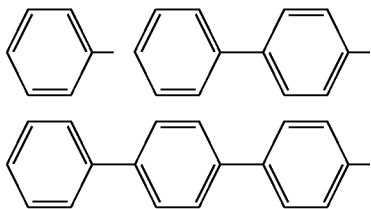

(IIIba) K=M=H and N=L and is selected from the group consisting of:

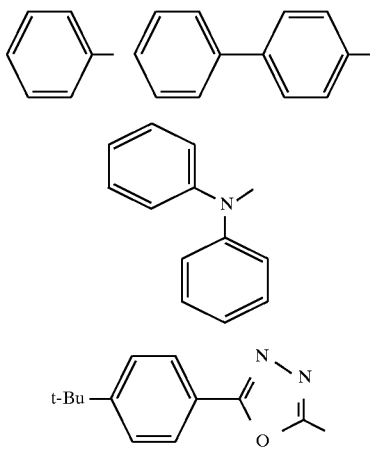

(IIIca) K=M and is selected from the group consisting of:

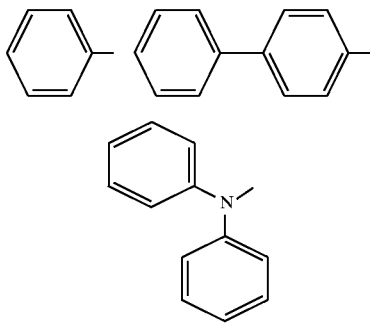

and N=L and is:

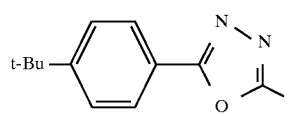

(IIIda) K=M and is selected from the group consisting of:

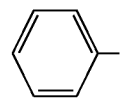

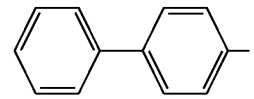

and N=L and is:

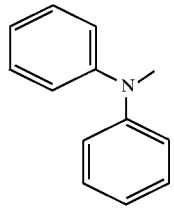

(IIIab) K=L=M=N and is selected from the group consisting of:

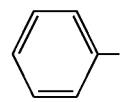

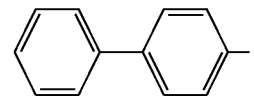

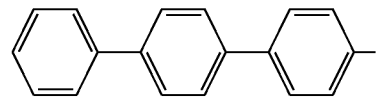

(IIIbb) K=L=H and M=N and is selected from the group consisting of:

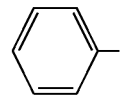

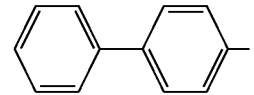

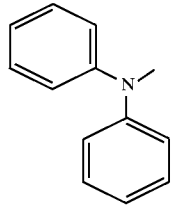

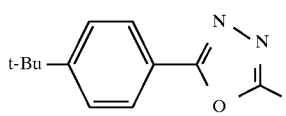

(IIIcb) K=L and is selected from the group consisting of:
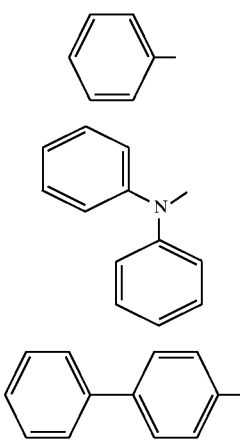
and M=N and is:
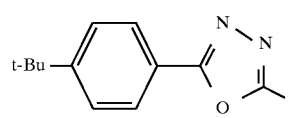
(IIIdb) K=L and is selected from the group consisting of:
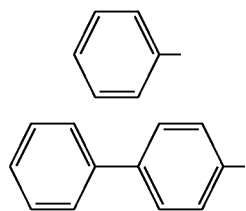
and M=N and is:
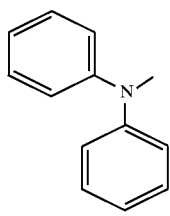
Very particularly preferred spiro compounds are those of the formula (IV)
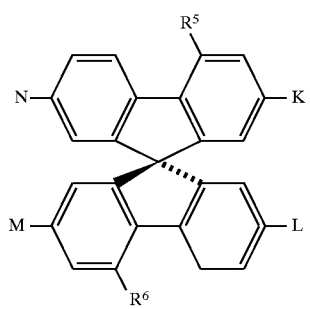
(IV)
where the symbols have the following meanings:
K R L, M, N, $R^5$, $R^6$ are identical or different and are one of the groups G1 to G14:
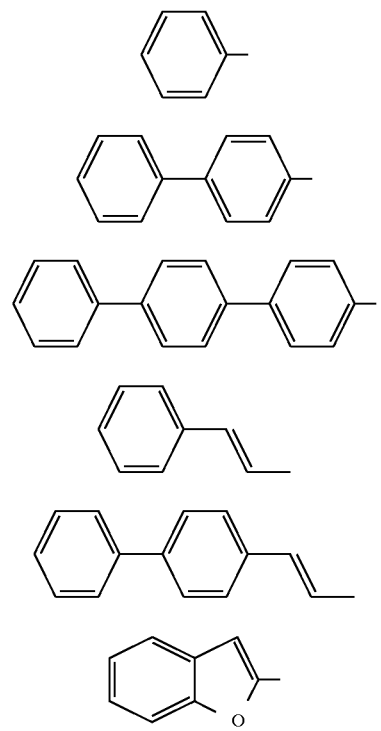
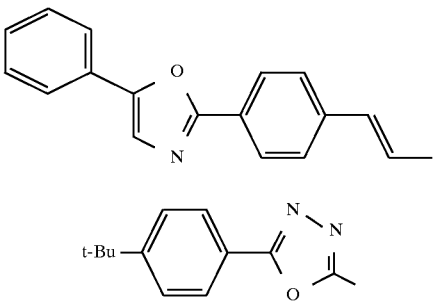

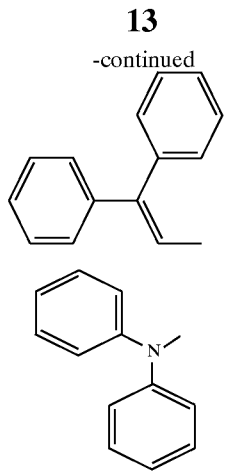

and $R^5_1$, $R^6$ can also be identical or different and be hydrogen or a linear or branched alkyl, alkyloxy or ester group having from 1 to 22 carbon atoms, —CN or —NO$_2$.

Most particularly preferred spiro compounds of the formula (IV) are 2,2',4,4',7,7'-hexakis(biphenylyl)-9,9'-spirobifluorene, 2,2',4,4',7,7'-hexakis(terphenylyl)-9,9'-spirobifluorene, and also the compounds shown in Table 1, in which the abbreviations G1 to G14 have the meanings given for the formula (IV).

TABLE 1

Spiro compounds of the formula (IV)
R5 = R6 = hydrogen

| Compound | K | L | M | N |
| --- | --- | --- | --- | --- |
| Spiro-1 | G1 | G1 | G3 | G3 |
| Spiro-2 | G1 | G1 | G4 | G4 |
| Spiro-3 | G1 | G1 | G5 | G5 |
| Spiro-4 | G1 | G1 | G6 | G6 |
| Spiro-5 | G1 | G1 | G7 | G7 |
| Spiro-6 | G1 | G1 | G8 | G8 |
| Spiro-7 | G1 | G1 | G9 | G9 |
| Spiro-8 | G1 | G1 | G10 | G10 |
| Spiro-9 | G1 | G1 | G11 | G11 |
| Spiro-10 | G1 | G1 | G12 | G12 |
| Spiro-11 | G1 | G1 | G13 | G13 |
| Spiro-12 | G1 | G1 | G14 | G14 |
| Spiro-13 | G2 | G2 | G2 | G2 |
| Spiro-14 | G2 | G2 | G3 | G3 |
| Spiro-15 | G2 | G2 | G4 | G4 |
| Spiro-16 | G2 | G2 | G5 | G5 |
| Spiro-17 | G2 | G2 | G6 | G6 |
| Spiro-16 | G2 | G2 | G7 | G7 |
| Spiro-19 | G2 | G2 | G8 | G8 |
| Spiro-20 | G2 | G2 | G9 | G9 |
| Spiro-21 | G2 | G2 | G10 | G10 |
| Spiro-22 | G2 | G2 | G11 | G11 |
| Spiro-23 | G2 | G2 | G12 | G12 |
| Spiro-24 | G2 | G2 | G13 | G13 |
| Spiro-25 | G2 | G2 | G14 | G14 |
| Spiro-26 | G3 | G3 | G3 | G3 |
| Spiro-27 | G3 | G3 | G4 | G4 |
| Spiro-28 | G3 | G3 | G5 | G5 |
| Spiro-29 | G3 | G3 | G6 | G6 |
| Spiro-30 | G3 | G3 | G7 | G7 |
| Spiro-31 | G3 | G3 | G8 | G8 |
| Spiro-32 | G3 | G3 | G9 | G9 |
| Spiro-33 | G3 | G3 | G10 | G10 |
| Spiro-34 | G3 | G3 | G11 | G11 |
| Spiro-35 | G3 | G3 | G12 | G12 |
| Spiro-36 | G3 | G3 | G13 | G13 |
| Spiro-37 | G3 | G3 | G14 | G14 |
| Spiro-38 | G4 | G4 | G4 | G4 |
| Spiro-39 | G5 | G5 | G5 | G5 |
| Spiro-40 | G6 | G6 | G6 | G6 |

TABLE 1-continued

Spiro compounds of the formula (IV)
R5 = R6 = hydrogen

| Compound | K | L | M | N |
| --- | --- | --- | --- | --- |
| Spiro-41 | G7 | G7 | G7 | G7 |
| Spiro-42 | G8 | G8 | G8 | G8 |
| Spiro-43 | G9 | G9 | G9 | G9 |
| Spiro-44 | G10 | G10 | G10 | G10 |
| Spiro-45 | G11 | G11 | G11 | G11 |
| Spiro-46 | G12 | G12 | G12 | G12 |
| Spiro-47 | G13 | G13 | G13 | G13 |
| Spiro-48 | G14 | G14 | G14 | G14 |
| Spiro-49 | H | H | G3 | G3 |
| Spiro-50 | H | H | G4 | G4 |
| Spiro-51 | H | H | G5 | G5 |
| Spiro-52 | H | H | G6 | G6 |
| Spiro-53 | H | H | G7 | G7 |
| Spiro-54 | H | H | G8 | G8 |
| Spiro-55 | H | H | G9 | G9 |
| Spiro-56 | H | H | G10 | G10 |
| Spiro-57 | H | H | G11 | G11 |
| Spiro-58 | H | H | G12 | G12 |
| Spiro-59 | H | H | G13 | G13 |
| Spiro-60 | H | H | G14 | G14 |
| Spiro-61 | G1 | G3 | G3 | G1 |
| Spiro-62 | G1 | G4 | G4 | G1 |
| Spiro-63 | G1 | G5 | G5 | G1 |
| Spiro-64 | G1 | G6 | G6 | G1 |
| Spirn-65 | G1 | G7 | G7 | G1 |
| Spiro-66 | G1 | G8 | G8 | G1 |
| Spiro-67 | G1 | G9 | G9 | G1 |
| Spiro-68 | G1 | G10 | G10 | G1 |
| Spiro-99 | G1 | G11 | G11 | G1 |
| Spiro-70 | G1 | G12 | G12 | G1 |
| Spiro-71 | G1 | G13 | G13 | G1 |
| Spiro-72 | G1 | G14 | G14 | G1 |
| Spiro-73 | G2 | G4 | G4 | G2 |
| Spiro-74 | G2 | G5 | G5 | G2 |
| Spiro-75 | G2 | G6 | G6 | G2 |
| Spiro-76 | G2 | G7 | G7 | G2 |
| Spiro-77 | G2 | G8 | G8 | G2 |
| Spiro-78 | G2 | G9 | G9 | G2 |
| Spiro-79 | G2 | G10 | G10 | G2 |
| Spiro-80 | G2 | G11 | G11 | G2 |
| Spiro-81 | G2 | G12 | G12 | G2 |
| Spiro-82 | G2 | G13 | G13 | G2 |
| Spiro-83 | G2 | G14 | G14 | G2 |
| Spiro-84 | G3 | G4 | G4 | G3 |
| Spiro-85 | G3 | G5 | G5 | G3 |
| Spiro-86 | G3 | G6 | G6 | G3 |
| Spiro-87 | G3 | G7 | G7 | G3 |
| Spiro-88 | G3 | G8 | G8 | G3 |
| Spiro-89 | G3 | G9 | G9 | G3 |
| Spiro-90 | G3 | G10 | G10 | G3 |
| Spiro-91 | G3 | G11 | G11 | G3 |
| Spiro-92 | G3 | G12 | G12 | G3 |
| Spiro-93 | G3 | G13 | G13 | G3 |
| Spiro-94 | G3 | G14 | G14 | G3 |
| Spiro-95 | H | G3 | G3 | H |
| Spiro-96 | H | G4 | G4 | H |
| Spiro-97 | H | G5 | G5 | H |
| Spiro-98 | H | G6 | G6 | H |
| Spiro-99 | H | G7 | G7 | H |
| Spiro-100 | H | G8 | G8 | H |
| Spiro-101 | H | G9 | G9 | H |
| Spiro-102 | H | G10 | G10 | H |
| Spiro-103 | H | G11 | G11 | H |
| Spiro-104 | H | G12 | G12 | H |
| Spiro-105 | H | G13 | G13 | H |
| Spiro-106 | H | G14 | G14 | H |

Some of the spiro compounds used according to the invention are known and some are new.

The invention accordingly also provides spiro compounds of the formula (V)

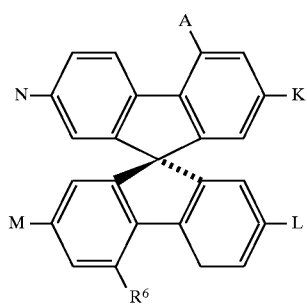

(V)

where the symbols have the following meanings:

A, B, K, L, M, N are identical or different and are

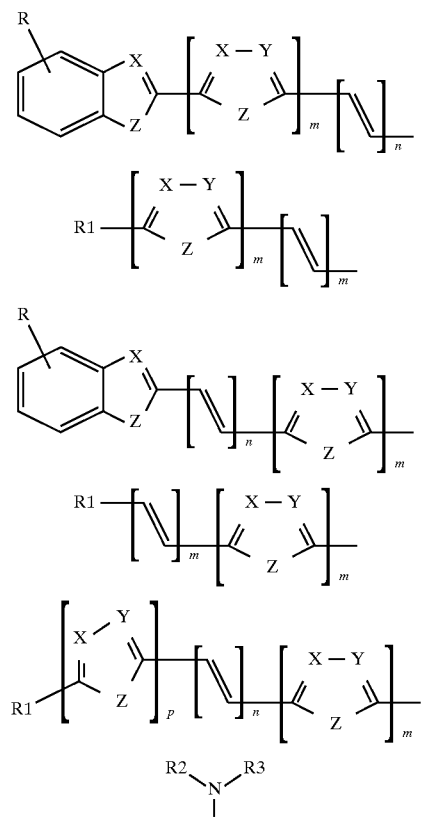

and A, B can also be identical or different and be a linear or branched alkyl, alkyloxy or ester group having from 1 to 22 carbon atoms, —CN, —NO$_2$, —Ar or —O—Ar;

R is H, a linear or branched alkyl, alkoxy or ester group having from 1 to 22, preferably from 1 to 15, particularly preferably from 1 to 12, carbon atoms, —CN, —NO$_2$, —NR$^2$R$^3$, —Ar or —O—Ar;

Ar is phenyl, biphenyl, 1-naphthyl, 2-naphthyl, 2-thienyl, 2-furyl, with each of these groups being able to bear one or two radicals R;

m, n, p are 0, 1, 2 or 3;

X, Y are identical or different and are CR, N;

Z is —O—, —S—, —NR$^1$—, —CR$^1$R$^4$—, —CH=CH—, —CH=N—;

R$^1$, R$^4$ can be identical or different and have the same meanings as R;

R$^2$, R$^3$ are identical or different and are H, a linear or branched alkyl group having from 1 to 22 carbon atoms, —Ar or 3-methylphenyl.

Preference is given to compounds of the formula (V) in which K, L, M, N and, if desired, A, B are selected from the following group G1 to G14:

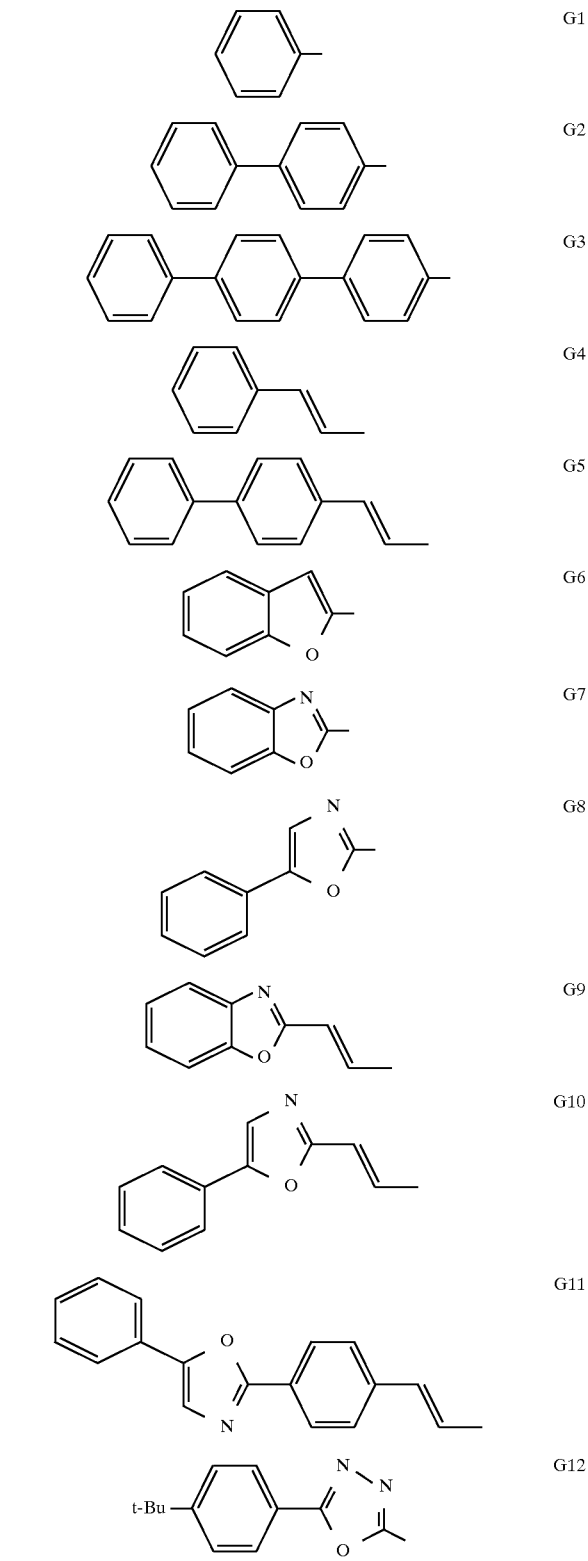

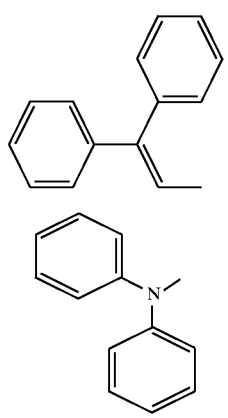

G13

G14

Most particularly preferred spiro compounds of the formula (V) are 2,2',4,4',7,7'-hexakis(biphenylyl)-9,9'-spirobifluorene, 2,2',4,4',7,7'-hexakis(terphenylyl)-9,9'-spirobifluorene, and also the compounds shown in Tables 2 and 5, where the abbreviations G1 to G14 have the same meanings as for the formula (V).

TABLE 2

Spiro compounds of the formula (V)
A = B = G1

| Compound | K | L | M | N |
|---|---|---|---|---|
| Spiro-107 | G1 | G1 | G3 | G3 |
| Spiro-108 | G1 | G1 | G4 | G4 |
| Spiro-109 | G1 | G1 | G5 | G5 |
| Spiro-110 | G1 | G1 | G6 | G6 |
| Spiro-111 | G1 | G1 | G7 | G7 |
| Spiro-112 | G1 | G1 | G8 | G8 |
| Spiro-113 | G1 | G1 | G9 | G9 |
| Spiro-114 | G1 | G1 | G10 | G10 |
| Spiro-115 | G1 | G1 | G11 | G11 |
| Spiro-116 | G1 | G1 | G12 | G12 |
| Spiro-117 | G1 | G1 | G13 | G13 |
| Spiro-118 | G1 | G1 | G14 | G14 |
| Spiro-119 | G2 | G2 | G2 | G2 |
| Spiro-120 | G2 | G2 | G3 | G3 |
| Spiro-121 | G2 | G2 | G4 | G4 |
| Spiro-122 | G2 | G2 | G5 | G5 |
| Spiro-123 | G2 | G2 | G6 | G6 |
| Spiro-124 | G2 | G2 | G7 | G7 |
| Spiro-125 | G2 | G2 | G8 | G8 |
| Spiro-126 | G2 | G2 | G9 | G9 |
| Spiro-127 | G2 | G2 | G10 | G10 |
| Spiro-128 | G2 | G2 | G11 | G11 |
| Spiro-129 | G2 | G2 | G12 | G12 |
| Spiro-130 | G2 | G2 | G13 | G13 |
| Spiro-131 | G2 | G2 | G14 | G14 |
| Spiro-132 | G3 | G3 | G3 | G3 |
| Spiro-133 | G3 | G3 | G4 | G4 |
| Spiro-134 | G3 | G3 | G5 | G5 |
| Spiro-135 | G3 | G3 | G6 | G6 |
| Spiro-136 | G3 | G3 | G7 | G7 |
| Spiro-137 | G3 | G3 | G8 | G8 |
| Spiro-138 | G3 | G3 | G9 | G9 |
| Spiro-139 | G3 | G3 | G10 | G10 |
| Spiro-140 | G3 | G3 | G11 | G11 |
| Spiro-141 | G3 | G3 | G12 | G12 |
| Spiro-142 | G3 | G3 | G13 | G13 |
| Spiro-143 | G3 | G3 | G14 | G14 |
| Spiro-144 | G4 | G4 | G4 | G4 |
| Spiro-145 | G5 | G5 | G5 | G5 |
| Spiro-146 | G6 | G6 | G6 | G6 |
| Spiro-147 | G7 | G7 | G7 | G7 |
| Spiro-148 | G8 | G8 | G8 | G8 |
| Spiro-149 | G9 | G9 | G9 | G9 |
| Spiro-150 | G10 | G10 | G10 | G10 |
| Spiro-151 | G11 | G11 | G11 | G11 |

TABLE 2-continued

Spiro compounds of the formula (V)
A = B = G1

| Compound | K | L | M | N |
|---|---|---|---|---|
| Spiro-152 | G12 | G12 | G12 | G12 |
| Spiro-153 | G13 | G13 | G13 | G13 |
| Spiro-154 | G14 | G14 | G14 | G14 |
| Spiro-155 | H | H | G3 | G3 |
| Spiro-156 | H | H | G4 | G4 |
| Spiro-157 | H | H | G5 | G5 |
| Spiro-158 | H | H | G6 | G6 |
| Spiro-159 | H | H | G7 | G7 |
| Spiro-160 | H | H | G8 | G8 |
| Spiro-161 | H | H | G9 | G9 |
| Spiro-162 | H | H | G10 | G10 |
| Spiro-163 | H | H | G11 | G11 |
| Spiro-164 | H | H | G12 | G12 |
| Spiro-165 | H | H | G13 | G13 |
| Spiro-166 | H | H | G14 | G14 |
| Spiro-167 | G1 | G3 | G3 | G1 |
| Spiro-168 | G1 | G4 | G4 | G1 |
| Spiro-169 | G1 | G5 | G5 | G1 |
| Spiro-170 | G1 | G6 | G6 | G1 |
| Spiro-171 | G1 | G7 | G7 | G1 |
| Spiro-172 | G1 | G8 | G8 | G1 |
| Spiro-173 | G1 | G9 | G9 | G1 |
| Spiro-174 | G1 | G10 | G10 | G1 |
| Spiro-175 | G1 | G11 | G11 | G1 |
| Spiro-176 | G1 | G12 | G12 | G1 |
| Spiro-177 | G1 | G13 | G13 | G1 |
| Spiro-178 | G1 | G14 | G14 | G1 |
| Spiro-179 | G2 | G4 | G4 | G2 |
| Spiro-180 | G2 | G5 | G5 | G2 |
| Spiro-181 | G2 | G6 | G6 | G2 |
| Spiro-182 | G2 | G7 | G7 | G2 |
| Spiro-183 | G2 | G8 | G8 | G2 |
| Spiro-184 | G2 | G9 | G9 | G2 |
| Spiro-185 | G2 | G10 | G10 | G2 |
| Spiro-186 | G2 | G11 | G11 | G2 |
| Spiro-187 | G2 | G12 | G12 | G2 |
| Spiro-188 | G2 | G13 | G13 | G2 |
| Spiro-189 | G2 | G14 | G14 | G2 |
| Spiro-190 | G3 | G4 | G4 | G3 |
| Spiro-191 | G3 | G5 | G5 | G3 |
| Spiro-192 | G3 | G6 | G6 | G3 |
| Spiro-193 | G3 | G7 | G7 | G3 |
| Spiro-194 | G3 | G8 | G8 | G3 |
| Spiro-195 | G3 | G9 | G9 | G3 |
| Spiro-196 | G3 | G10 | G10 | G3 |
| Spiro-197 | G3 | G11 | G11 | G3 |
| Spiro-198 | G3 | G12 | G12 | G3 |
| Spiro-199 | G3 | G13 | G13 | G3 |
| Spiro-200 | G3 | G14 | G14 | G3 |
| Spiro-201 | H | G3 | G3 | H |
| Spiro-202 | H | G4 | G4 | H |
| Spiro-203 | H | G5 | G5 | H |
| Spiro-204 | H | G6 | G6 | H |
| Spiro-205 | H | G7 | G7 | H |
| Spiro-206 | H | G8 | G8 | H |
| Spiro-207 | H | G9 | G9 | H |
| Spiro-208 | H | G10 | G10 | H |
| Spiro-209 | H | G11 | G11 | H |
| Spiro-210 | H | G12 | G12 | H |
| Spiro-211 | H | G13 | G13 | H |
| Spiro-212 | H | G14 | G14 | H |

TABLE 3

Spiro compounds of the formula (V)
A = B = G2

| Compound | K | L | M | N |
|---|---|---|---|---|
| Spiro-213 | G1 | G1 | G3 | G3 |
| Spiro-214 | G1 | G1 | G4 | G4 |
| Spiro-215 | G1 | G1 | G5 | G5 |

TABLE 3-continued

Spiro compounds of the formula (V)
A = B = G2

| Compound | K | L | M | N |
|---|---|---|---|---|
| Spiro-216 | G1 | G1 | G6 | G6 |
| Spiro-217 | G1 | G1 | G7 | G7 |
| Spiro-218 | G1 | G1 | G8 | G8 |
| Spiro-219 | G1 | G1 | G9 | G9 |
| Spiro-220 | G1 | G1 | G10 | G10 |
| Spiro-221 | G1 | G1 | G11 | G11 |
| Spiro-222 | G1 | G1 | G12 | G12 |
| Spir6-223 | G1 | G1 | G13 | G13 |
| Spiro-224 | G1 | G1 | G14 | G14 |
| Spiro-225 | G2 | G2 | G2 | G2 |
| Spiro-226 | G2 | G2 | G3 | G3 |
| Spiro-227 | G2 | G2 | G4 | G4 |
| Spiro-228 | G2 | G2 | G5 | G5 |
| Spiro-229 | G2 | G2 | G6 | G6 |
| Spiro-230 | G2 | G2 | G7 | G7 |
| Spiro-231 | G2 | G2 | G8 | G8 |
| Spiro-232 | G2 | G2 | G9 | G9 |
| Spiro-233 | G2 | G2 | G10 | G10 |
| Spiro-234 | G2 | G2 | G11 | G11 |
| Spiro-235 | G2 | G2 | G12 | G12 |
| Spiro-236 | G2 | G2 | G13 | G13 |
| Spiro-237 | G2 | G2 | G14 | G14 |
| Spiro-238 | G3 | G3 | G3 | G3 |
| Spiro-239 | G3 | G3 | G4 | G4 |
| Spiro-240 | G3 | G3 | G5 | G5 |
| Spiro-241 | G3 | G3 | G6 | G6 |
| Spiro-242 | G3 | G3 | G7 | G7 |
| Spiro-243 | G3 | G3 | G8 | G8 |
| Spiro-244 | G3 | G3 | G9 | G9 |
| Spiro-245 | G3 | G3 | G10 | G10 |
| Spiro-246 | G3 | G3 | G11 | G11 |
| Spiro-247 | G3 | G3 | G12 | G12 |
| Spiro-248 | G3 | G3 | G13 | G13 |
| Spiro-249 | G3 | G3 | G14 | G14 |
| Spiro-250 | G4 | G4 | G4 | G4 |
| Spiro-251 | G5 | G5 | G5 | G5 |
| Spiro-252 | G6 | G6 | G6 | G6 |
| Spiro-253 | G7 | G7 | G7 | G7 |
| Spiro-254 | G8 | G8 | G8 | G8 |
| Spiro-255 | G9 | G9 | G9 | G9 |
| Spiro-256 | G10 | G10 | G10 | G10 |
| Spiro-257 | G11 | G11 | G11 | G11 |
| Spiro-258 | G12 | G12 | G12 | G12 |
| Spiro-259 | G13 | G13 | G13 | G13 |
| Spiro-260 | G14 | G14 | G14 | G14 |
| Spiro-261 | H | H | G3 | G3 |
| Spiro-262 | H | H | G4 | G4 |
| Spiro-263 | H | H | G5 | G5 |
| Spiro-264 | H | H | G6 | G6 |
| Spiro-265 | H | H | G7 | G7 |
| Spiro-266 | H | H | G8 | G8 |
| Spiro-267 | H | H | G9 | G9 |
| Spiro-268 | H | H | G10 | G10 |
| Spiro-269 | H | H | G11 | G11 |
| Spiro-270 | H | H | G12 | G12 |
| Spiro-271 | H | H | G13 | G13 |
| Spiro-272 | H | H | G14 | G14 |
| Spiro-273 | G1 | G3 | G3 | G1 |
| Spiro-274 | G1 | G4 | G4 | G1 |
| Spiro-275 | G1 | G5 | G5 | G1 |
| Spiro-276 | G1 | G6 | GG | G1 |
| Spiro-277 | G1 | G7 | G7 | G1 |
| Spiro-278 | G1 | G8 | G8 | G1 |
| Spiro-279 | G1 | G9 | G9 | G1 |
| Spiro-280 | G1 | G10 | G10 | G1 |
| Spiro-281 | G1 | G11 | G11 | G1 |
| Spiro-282 | G1 | G12 | G12 | G1 |
| Spiro-283 | G1 | G13 | G13 | G1 |
| Spiro-284 | G1 | G14 | G14 | G1 |
| Spiro-285 | G2 | G4 | G4 | G2 |
| Spiro-286 | G2 | G5 | G5 | G2 |
| Spiro-287 | G2 | G6 | G6 | G2 |
| Spiro-288 | G2 | G7 | G7 | G2 |
| Spiro-289 | G2 | G8 | G8 | G2 |
| Spiro-290 | G2 | G9 | G9 | G2 |
| Spiro-291 | G2 | G10 | G10 | G2 |
| Spiro-292 | G2 | G11 | G11 | G2 |
| Spiro-293 | G2 | G12 | G12 | G2 |
| Spiro-294 | G2 | G13 | G13 | G2 |
| Spiro-295 | G2 | G14 | G14 | G2 |
| Spiro-296 | G3 | G4 | G4 | G3 |
| Spiro-297 | G3 | G5 | G5 | G3 |
| Spiro-298 | G3 | G6 | G6 | G3 |
| Spiro-299 | G3 | G7 | G7 | G3 |
| Spiro-300 | G3 | G8 | G8 | G3 |
| Spiro-301 | G3 | G9 | G9 | G3 |
| Spiro-302 | G3 | G10 | G10 | G3 |
| Spiro-303 | G3 | G11 | G11 | G3 |
| Spiro-304 | G3 | G12 | G12 | G3 |
| Spiro-305 | G3 | G13 | G13 | G3 |
| Spiro-306 | G3 | G14 | G14 | G3 |
| Spiro-307 | H | G3 | G3 | H |
| Spiro-308 | H | G4 | G4 | H |
| Spiro-309 | H | G5 | G5 | H |
| Spiro-310 | H | G6 | G6 | H |
| Spiro-311 | H | G7 | G7 | H |
| Spiro-312 | H | G8 | G8 | H |
| Spiro-313 | H | G9 | G9 | H |
| Spiro-314 | H | G10 | G10 | H |
| Spiro-315 | H | G11 | G11 | H |
| Spiro-316 | H | G12 | G12 | H |
| Spiro-317 | H | G13 | G13 | H |
| Spiro-318 | H | G14 | G14 | H |

TABLE 4

Spiro compounds of the formula (V)
A = B = G3

| Compound | K | L | M | N |
|---|---|---|---|---|
| Spiro-319 | G1 | G1 | G3 | G3 |
| Spiro-320 | G1 | G1 | G4 | G4 |
| Spiro-321 | G1 | G1 | G5 | G5 |
| Spiro-322 | G1 | G1 | G6 | G6 |
| Spiro-323 | G1 | G | G7 | G7 |
| Spiro-324 | G1 | G | G8 | G8 |
| Spiro-325 | G1 | G1 | G9 | G9 |
| Spiro-326 | G1 | G1 | G10 | G10 |
| Spiro-327 | G1 | G1 | G11 | G11 |
| Spiro-328 | G1 | G1 | G12 | G12 |
| Spiro-329 | G1 | G1 | G13 | G13 |
| Spiro-330 | G1 | G1 | G14 | G14 |
| Spiro-331 | G2 | G2 | G2 | G2 |
| Spiro-332 | G2 | G2 | G3 | G3 |
| Spiro-333 | G2 | G2 | G4 | G4 |
| Spiro-334 | G2 | G2 | G5 | G5 |
| Spiro-335 | G2 | G2 | G6 | G6 |
| Spiro-336 | G2 | G2 | G7 | G7 |
| Spiro-337 | G2 | G2 | G8 | G8 |
| Spiro-338 | G2 | G2 | G9 | G9 |
| Spiro-339 | G2 | G2 | G10 | G10 |
| Spiro-340 | G2 | G2 | G11 | G11 |
| Spiro-341 | G2 | G2 | G12 | G12 |
| Spiro-342 | G2 | G2 | G13 | G13 |
| Spiro-343 | G2 | G2 | G14 | G14 |
| Spiro-344 | G3 | G3 | G3 | G3 |
| Spiro-345 | G3 | G3 | G4 | G4 |
| Spiro-346 | G3 | G3 | G5 | G5 |
| Spiro-347 | G3 | G3 | G6 | G6 |
| Spiro-348 | G3 | G3 | G7 | G7 |
| Spiro-349 | G3 | G3 | G8 | G8 |
| Spiro-350 | G3 | G3 | G9 | G9 |
| Spiro-351 | G3 | G3 | G10 | G10 |
| Spiro-352 | G3 | G3 | G11 | G11 |

TABLE 4-continued

Spiro compounds of the formula (V)
A = B = G3

| Compound | K | L | M | N |
|---|---|---|---|---|
| Spiro-353 | G3 | G3 | G12 | G12 |
| Spiro-354 | G3 | G3 | G13 | G13 |
| Spiro-355 | G3 | G3 | G14 | G14 |
| Spiro-356 | G4 | G4 | G4 | G4 |
| Spiro-357 | G5 | G5 | G5 | G5 |
| Spiro-358 | G6 | G6 | G6 | G6 |
| Spiro-359 | G7 | G7 | G7 | G7 |
| Spiro-360 | G8 | G8 | G8 | G8 |
| Spiro-361 | G9 | G9 | G9 | G9 |
| Spiro-362 | G10 | G10 | G10 | G10 |
| Spiro-363 | G11 | G11 | G11 | G11 |
| Spiro-364 | G12 | G12 | G12 | G12 |
| Spiro-365 | G13 | G13 | G13 | G13 |
| Spiro-366 | G14 | G14 | G14 | G14 |
| Spiro-367 | H | H | G3 | G3 |
| Spiro-368 | H | H | G4 | G4 |
| Spiro-369 | H | H | G5 | G5 |
| Spiro-370 | H | H | G6 | G6 |
| Spiro-371 | H | H | G7 | G7 |
| Spiro-372 | H | H | G8 | G8 |
| Spiro-373 | H | H | G9 | G9 |
| Spiro-374 | H | H | G10 | G10 |
| Spiro-375 | H | H | G11 | G11 |
| Spiro-376 | H | H | G12 | G12 |
| Spiro-377 | H | H | G13 | G13 |
| Spiro-378 | H | H | G14 | G14 |
| Spiro-379 | G1 | G3 | G3 | G1 |
| Spiro-380 | G1 | G4 | G4 | G1 |
| Spiro-381 | G1 | G5 | G5 | G1 |
| Spiro-382 | G1 | G6 | G6 | G1 |
| Spiro-383 | G1 | G7 | G7 | G1 |
| Spiro-384 | G1 | G8 | G8 | G1 |
| Spiro-385 | G1 | G9 | G9 | G1 |
| Spiro-386 | G1 | G10 | G10 | G1 |
| Spiro-387 | G1 | G11 | G11 | G1 |
| Spiro-388 | G1 | G12 | G12 | G1 |
| spiro-389 | G1 | G13 | G13 | G1 |
| Spiro-390 | G1 | G14 | G14 | G1 |
| Spiro-391 | G2 | G4 | G4 | G2 |
| Spiro-392 | G2 | G5 | G5 | G2 |
| Spiro-393 | G2 | G6 | G6 | G2 |
| Spiro-394 | G2 | G7 | G7 | G2 |
| Spiro-395 | G2 | G8 | G8 | G2 |
| Spiro-396 | G2 | G9 | G9 | G2 |
| Spiro-397 | G2 | G10 | G10 | G2 |
| Spiro-398 | G2 | G11 | G11 | G2 |
| Spiro-399 | G2 | G12 | G12 | G2 |
| Spiro-400 | G2 | G13 | G13 | G2 |
| Spiro-401 | G2 | G14 | G14 | G2 |
| Spiro-402 | G3 | G4 | G4 | G3 |
| Spiro-403 | G3 | G5 | G5 | G3 |
| Spiro-404 | G3 | G6 | G6 | G3 |
| Spiro-405 | G3 | G7 | G7 | G3 |
| Spiro-406 | G3 | G8 | G8 | G3 |
| Spiro-407 | G3 | G9 | G9 | G3 |
| Spiro-408 | G3 | G10 | G10 | G3 |
| Spiro-409 | G3 | G11 | G11 | G3 |
| Spifo-410 | G3 | G12 | G12 | G3 |
| Spiro-411 | G3 | G13 | G13 | G3 |
| Spiro-412 | G3 | G14 | G14 | G3 |
| Spiro-413 | H | G3 | G3 | H |
| Spiro-414 | H | G4 | G4 | H |
| Spiro-415 | H | G5 | G5 | H |
| Spiro-416 | H | G6 | G6 | H |
| Spiro-417 | H | G7 | G7 | H |
| Spiro-418 | H | G8 | G8 | H |
| Spiro-419 | H | G9 | G9 | H |
| Spiro-420 | H | G10 | G10 | H |
| Spiro-421 | H | G11 | G11 | H |
| Spiro-422 | H | G12 | G12 | H |
| Spiro-423 | H | G13 | G13 | H |
| Spiro-424 | H | G14 | G14 | H |

TABLE 5

Spiro compounds of the formula (V)
A = B = G12

| Compound | K | L | M | N |
|---|---|---|---|---|
| Spiro-425 | G1 | G1 | G3 | G3 |
| Spiro-426 | G1 | G1 | G4 | G4 |
| Spiro-427 | G1 | G1 | G5 | G5 |
| Spiro-428 | G1 | G1 | G6 | G6 |
| Spiro-429 | G1 | G1 | G7 | G7 |
| Spiro-430 | G1 | G1 | G8 | G8 |
| Spiro-431 | G1 | G1 | G9 | G9 |
| Spiro-432 | G1 | G1 | G10 | G10 |
| Spiro-433 | G1 | G1 | G11 | G11 |
| Spiro-434 | G1 | G1 | G12 | G12 |
| Spiro-435 | G1 | G1 | G13 | G13 |
| Spiro-436 | G1 | G1 | G14 | G14 |
| Spiro-437 | G2 | G2 | G2 | G2 |
| Spiro-438 | G2 | G2 | G3 | G3 |
| Spiro-439 | G2 | G2 | G4 | G4 |
| Spiro-440 | G2 | G2 | G5 | G5 |
| Spiro-441 | G2 | G2 | G6 | G6 |
| Spiro-442 | G2 | G2 | G7 | G7 |
| Spiro-443 | G2 | G2 | G8 | G8 |
| Spiro-444 | G2 | G2 | G9 | G9 |
| Spiro-445 | G2 | G2 | G10 | G10 |
| Spiro-446 | G2 | G2 | G11 | G11 |
| Spiro-447 | G2 | G2 | G12 | G12 |
| Spiro-448 | G2 | G2 | G13 | G13 |
| Spiro-449 | G2 | G2 | G14 | G14 |
| Spiro-450 | G3 | G3 | G3 | G3 |
| Spiro-451 | G3 | G3 | G4 | G4 |
| Spiro-452 | G3 | G3 | G5 | G5 |
| Spiro-453 | G3 | G3 | G6 | G6 |
| Spiro-454 | G3 | G3 | G7 | G7 |
| Spiro-455 | G3 | G3 | G8 | G8 |
| Spiro-456 | G3 | G3 | G9 | G9 |
| Spiro-457 | G3 | G3 | G10 | G10 |
| Spiro-458 | G3 | G3 | G11 | G11 |
| Spiro-459 | G3 | G3 | G12 | G12 |
| Spiro-460 | G3 | G3 | G13 | G13 |
| Spiro-461 | G3 | G3 | G14 | G14 |
| Spiro-462 | G4 | G4 | G4 | G4 |
| Spiro-463 | G5 | G5 | G5 | G5 |
| Spiro-464 | G6 | G6 | G6 | G6 |
| Spiro-465 | G7 | G7 | G7 | G7 |
| Spiro-466 | G8 | G8 | G8 | G8 |
| Spiro-467 | G9 | G9 | G9 | G9 |
| Spiro-468 | G10 | G10 | G10 | G10 |
| Spiro-469 | G11 | G11 | G11 | G11 |
| Spiro-470 | G12 | G12 | G12 | G12 |
| Spiro-471 | G13 | G13 | G13 | G13 |
| Spiro-472 | G14 | G14 | G14 | G14 |
| Spiro-473 | H | H | G3 | G3 |
| Spiro-474 | H | H | G4 | G4 |
| Spiro-475 | H | H | G5 | G5 |
| Spiro-476 | H | H | G6 | G6 |
| Spiro-477 | H | H | G7 | G7 |
| Spiro-478 | H | H | G8 | G8 |
| Spiro-479 | H | H | G9 | G9 |
| Spiro-480 | H | H | G10 | G10 |
| Spiro-481 | H | H | G11 | G11 |
| Spiro-482 | H | H | G12 | G12 |
| Spiro-483 | H | H | G13 | G13 |
| Spiro-484 | H | H | G14 | G14 |
| Spiro-485 | G1 | G3 | G3 | G1 |
| Spiro-486 | G1 | G4 | G4 | G1 |
| Spiro-487 | G1 | G5 | G5 | G1 |
| Spiro-488 | G1 | G6 | G6 | G1 |
| Spiro-489 | G1 | G7 | G7 | G1 |
| Spiro-490 | G1 | G8 | G8 | G1 |
| Spiro-491 | G1 | G9 | G9 | G1 |
| Spiro-492 | G1 | G10 | G10 | G1 |
| Spiro-493 | G1 | G11 | G11 | G1 |
| Spiro-494 | G1 | G12 | G12 | G1 |
| Spiro-495 | G1 | G13 | G13 | G1 |
| Spiro-496 | G1 | G14 | G14 | G1 |
| Spiro-497 | G2 | G4 | G4 | G2 |
| Spiro-498 | G2 | G5 | G5 | G2 |

TABLE 5-continued

Spiro compounds of the formula (V)
A = B = G12

| Compound | K | L | M | N |
|---|---|---|---|---|
| Spiro-499 | G2 | G6 | G6 | G2 |
| Spiro-500 | G2 | G7 | G7 | G2 |
| Spiro-501 | G2 | G8 | G8 | G2 |
| Spiro-502 | G2 | G9 | G9 | G2 |
| Spiro-503 | G2 | G10 | G10 | G2 |
| Spiro-504 | G2 | G11 | G11 | G2 |
| Spiro-505 | G2 | G12 | G12 | G2 |
| Spiro-506 | G2 | G13 | G13 | G2 |
| Spiro-507 | G2 | G14 | G14 | G2 |
| Spiro-508 | G3 | G4 | G4 | G3 |
| Spiro-509 | G3 | G5 | G5 | G3 |
| Spiro-510 | G3 | G6 | G6 | G3 |
| Spiro-511 | G3 | G7 | G7 | G3 |
| Spiro-512 | G3 | G8 | G8 | G3 |
| Spiro-513 | G3 | G9 | G9 | G3 |
| Spiro-514 | G3 | G10 | G10 | G3 |
| Spiro-515 | G3 | G11 | G11 | G3 |
| Spiro-516 | G3 | G12 | G12 | G3 |
| Spiro-517 | G3 | G13 | G13 | G3 |
| Spiro-518 | G3 | G14 | G14 | G3 |
| Spiro-519 | H | G3 | G3 | H |
| Spiro-520 | H | G4 | G4 | H |
| Spiro-521 | H | G5 | G5 | H |
| Spiro-522 | H | G6 | G6 | H |
| Spiro-523 | H | G7 | G7 | H |
| Spiro-524 | H | G8 | G8 | H |
| Spiro-525 | H | G9 | G9 | H |
| Spiro-526 | H | G10 | G10 | H |
| Spiro-527 | H | G11 | G11 | H |
| Spiro-528 | H | G12 | G12 | H |
| Spiro-529 | H | G13 | G13 | H |
| Spiro-530 | H | G14 | G14 | H |

The spiro compounds used according to the invention are prepared by methods which are known per se in the literature, as are described in standard works on organic synthesis, e.g. Houben-Weyl, Methoden der Organischen Chemie [methods of organic chemistry], Georg-Thieme-Verlag, Stuttgart and in the appropriate volumes of the series "The Chemistry of Heterocyclic Compounds" by A. Weissberger and E. C. Taylor (editors).

The preparation is here carried out under reaction conditions which are known and suitable for said reactions. Use can also be made of variants which are known per se and are not mentioned in more detail here.

Compounds of the formula (III) are obtained, for example, starting from 9,9'-spirobifluorene whose synthesis is described, for example, by R. G. Clarkson, M. Gomberg, J. Am. Chem. Soc. 52 (1930) 2881.

The compounds of the formula (IIIa) can be prepared, for example, starting with a tetrahalogenation of the 9,9'-spirobifluorene in the 2,2',7,7' positions and a subsequent substitution reaction (see, for example, U.S. Pat. No. 5,026,894) or via a tetraacetylation of the 9,9'-spirobifluorene in the 2,2',7,7' positions with subsequent C—C linkage after conversion of the acetyl groups into aldehyde groups or heterocycle formation after conversion of the acetyl groups into carboxylic acid groups.

The compounds of the formula (IIIb) can be prepared, for example, by a similar method to those of the formula IIIa, with the stoichiometric ratios in the reaction being selected in such a way that the 2,2' or 7,7' positions are functionalized (see, for example, J. H. Weisburger, E. K. Weisburger, F. E. Ray, J. Am. Chem. Soc. 72 (1959) 4253; F. K. Sutcliffe, H. M. Shahidi, D. Paterson, J. Soc. Dyers Colour 94 (1978) 306 and G. Haas, V. Prelog, Helv. Chim. Acta 52 (1069) 1202).

The compounds of the formula (IIIc) can be prepared, for example, by dibromination in the 2,2' positions and subsequent diacetylation in the 7,7' positions of the 9,9'-spirobifluorene and subsequent reaction by a similar method to that for the compounds IIIa.

Compounds of the formulae (IIIe)–(IIIg) can be prepared, for example, by selection of suitably substituted starting compounds in the buildup of the spirobifluorene, e.g. 2,7-dibromospirobifluorene can be built up from 2,7-dibromofluorenone and 2,7-dicarbethoxy-9,9'-spirobifluorene by use of 2,7-dicarbethoxyfluorenone. The free 2',7' positions of the spirobifluorene can then be independently further substituted.

For the synthesis of the groups K, L, M, N, reference may be made, for example, to DE-A 23 44 732, 24 50 088, 24 29 093, 25 02 904, 26 36 684, 27 01 591 and 27 52 975 for compounds having 1,4-phenylene groups; DE A 26 41 724 for compounds having pyrimidine-2,5-diyl groups; DE-A 40 26 223 and EP-A 03 91 203 for compounds having pyridine-2,5-diyl groups; DE-A 32 31 462 for compounds having pyridazine-3,6-diyl groups; N. Miyaura, T. Yanagi and A. Suzuki in Synthetic Communications 11 (1981) 513 to 519, DE-A 3,930,663, M. J. Sharp, W. Cheng, V. Snieckus in Tetrahedron Letters 28 (1987), 5093; G. W. Gray in J. Chem. Soc. Perkin Trans II (1989) 2041 and Mol. Cryst. Liq. Cryst. 172 (1989) 165, Mol. Cryst. Liq. Cryst. 204 (1991) 43 and 91; EP-A 0,449,015; WO 89/12039; WO 89/03821; EP-A 0,354,434 for the direct linking of aromatics and heteroaromatics.

The preparation of disubstituted pyridines, disubstituted pyrazines, disubstituted pyrimidines and disubstituted pyridazines is given, for example, in the appropriate volumes of the series "The Chemistry of Heterocyclic Compounds" by A. Weissberger and E. C. Taylor (editors).

According to the invention, the spiro compounds described of the formulae (I), (II) and (III) are used as electroluminescence materials, i.e. they are used as active layer in an electroluminescence device. For the purposes of the invention, an active layer is an electroluminescence material which is capable of radiating light on application of an electric field (light-emitting material, light-emitting layer), and also a material which improves the injection (charge-injection material, charge-injection layer) and/or the transport of the positive and/or negative charges (charge-transport material, charge-transport layer).

Electroluminescence materials according to the invention have, inter alia, an exceptional temperature stability in comparison with known organic electroluminescence materials. This is shown, for example, by the emission maximum of the compounds decreasing only slightly, in other cases not at all, after thermal stressing and by many compounds even exhibiting an increase in the emission maximum after thermal stressing.

The invention accordingly also provides an organic electroluminescence material whose emission maximum in the range from 400 to 750 nm, measured at room temperature, is reduced by not more than 15% relative to the initial state, after the material, applied in a thickness of not more than 1 μm to a quartz substrate, has been heated at 250° C. for 30 minutes in an inert atmosphere at a pressure of not more than 1 mbar.

The reduction in the emission maximum is preferably not more than 10%, particularly preferably 5%, relative to the initial state before thermal treatment.

Very particular preference is given to electroluminescence materials which show no reduction in the emission maximum under the abovementioned conditions.

Most particularly preferred are those organic electroluminescence materials which show an increase in the emission maximum under the specified conditions.

An inert atmosphere is understood as meaning preferably a nitrogen or argon atmosphere.

The invention accordingly also provides an electroluminescence device having one or more active layers comprising one or more compounds of the formulae (I); (II) and/or (III). The active layer can be, for example, a light-emitting layer and/or a transport layer and/or a charge-injection layer.

The general structure of such electroluminescence devices is described, for example in U.S. Pat. No. 4,539,507 and U.S. Pat. No. 5,151,629.

They usually comprise an electroluminescing layer between a cathode and an anode, with at least one of the electrodes being transparent. In addition, an electron-injection and/or electron-transport layer can be introduced between the electroluminescing layer and the cathode, and/or a hole-injection and/or hole-transport layer can be introduced between the electroluminescing layer and the anode. Suitable cathodes are, for example, Ca, Mg, Al, In, Mg/Ag. Suitable anodes are, for example, Au or ITO (indium oxide/tin oxide on a transparent substrate, for example of glass or a transparent polymer).

In operation, the cathode is placed at a negative potential in comparison with the anode, injecting electrons from the cathode into the electron-injection layer/electron-transport layer or directly into the light-emitting layer. At the same time, holes from the anode are injected into the hole-injection layer/hole-transport layer or directly into the light-emitting layer.

The injected charge carriers move through the active layers toward one another under the action of the applied potential. At the interface between the charge-transport layer and the light-emitting layer or within the light-emitting layer this leads to electron/hole pairs which recombine with emission of light.

The color of the light emitted can be varied by means of the compound used as light-emitting layer.

Electroluminescence devices are used, for example, as self-illuminating display elements such as control lamps, alphanumeric displays, information signs, and in opto-electronic couplers.

The invention is illustrated by the examples, without being limited to them.

EXAMPLES

A. Starting compounds a) Synthesis of 9,9'-spirobifluorene 6.3 g of magnesium turnings and 50 mg of anthracene are initially placed in 120 ml of dry diethyl ether under argon in a 1 l three-necked flask fitted with reflux condenser and the magnesium is activated for 15 minutes using ultrasound.

62 g of 2-bromobiphenyl are dissolved in 60 ml of dry diethyl ether. About 10 ml of this solution are added to the initially charged magnesium to initiate the Grignard reaction.

After the reaction starts, the 2-bromobiphenyl solution is added dropwise with a further ultrasound treatment in such a way that the solution gently boils under reflux. After the addition is complete, the reaction mixture is boiled under reflux for a further hour with ultrasound.

48.8 g of 9-fluorenone are dissolved in 400 ml of dry diethyl ether and, with further ultrasound treatment, are added dropwise to the Grignard solution. After the addition is complete, the mixture is boiled for a further 2 hours. The yellow magnesium complex of 9-(2-biphenyl)-9-fluorenol precipitated after cooling the reaction mixture is filtered off with suction and washed with a little ether. The magnesium complex is hydrolyzed in 800 ml of ice water containing 40 g of ammonium chloride. After stirring for 60 minutes, the 9-(2-biphenyl)-9-fluorenol formed is filtered off with suction, washed with water and sucked dry.

The dried 9-(2-biphenyl)-9-fluorenol is then dissolved hot in 500 ml of glacial acetic acid. 0.5 ml of concentrated hydrochloric acid is added to this solution. The solution is allowed to boil for a few minutes and the 9,9'-spirobifluorene formed is precipitated from the hot solution using water (water added until the solution starts to become turbid). After cooling, the product is filtered off with suction and washed with water. The dried product is further purified by recrystallization from ethanol. This gives 66 g (80%, based on 2-bromobiphenyl) of 9,9'-spirobifluorene as colorless crystals, m.p. 198° C.

b) 2,2'-Dibromo-9,9'-spirobifluorene (F. K. Sutcliffe, H. M. Shahidi, D. Patterson, J. Soc. Dyers Colour 94 (1978) 306)

3.26 g (10.3 mmol) of 9,9,-spirobifluorene are dissolved in 30 ml of methylene chloride and admixed with 5 mg of $FeCl_3$ (anhydrous) as catalyst. The reaction flask is protected from light. 1.12 ml (21.8 mmol) of bromine in 5 ml of methylene chloride are added dropwise over a period of 30 minutes while stirring. After 24 hours, the resulting brown solution is washed with saturated aqueous $NaHCO_3$ solution and water to remove excess bromine. The organic phase is, after drying over $Na_2SO_4$, evaporated on a rotary evaporator. The white residue is recrystallized from methanol, giving 3.45 g (70%) of the dibromo compound as colorless crystals, m.p. 240° C.

c) 2,2',7,7'-Tetrabromo-9,9'-spirobifluorene 80 mg (0.5 mmol) of anhydrous $FeCl_3$ are added to a solution of 3.16 g (10.0 mmol) of 9,9'-spirobifluorene in 30 ml of methylene chloride, and 2.1 ml (41 mmol) of bromine in 5 ml of methylene chloride are added dropwise over a period of 10 minutes. The solution is refluxed for 6 hours. On cooling, the product precipitates. The precipitate is filtered off with suction and washed with a little cold methylene chloride. After drying, 6.0 g (95%) of the tetrabromo compound are obtained as a white solid.

d) 2-Bromo-9,9'-spirobifluorene and 2,2',7-tribromo-9,9'-spirobifluorene can be prepared in a similar manner using different stoichiometry.

e) 9,9'-Spirobifluorene-2,2'-dicarboxylic acid from 2,2'-dibromo-9,9'-spirobifluorene via 2,2'-dicyano-9,9'-spirobifluorene 1.19 g of 2,2'-dibromo-9,9'-spirobifluorene and 0.54 g of CuCN are heated under reflux in 5 ml of DMF for 6 hours. The brown mixture obtained is poured into a mixture of 3 g of $FeCl_3$ (hydrated) and 1.5 ml of concentrated hydrochloric acid in 20 ml of water. The mixture is maintained at from 60° to 70° C. for 30 minutes, to destroy the Cu complex. The hot aqueous solution is extracted twice with toluene. The organic phases are then washed with dilute hydrochloric acid, water and 10% strength aqueous NaOH. The organic phase is filtered and evaporated. The yellow residue obtained is recrystallized from methanol. This gives 0.72 g (80%) of 2,2'-dicyano-9,9'-spirobifluorene as pale yellow crystals (melting range from 215° to 245° C.).

3 g of 2,2'-dicyano-9,9'-spirobifluorene are heated under reflux with 25 ml of 30% strength aqueous NaOH and 30 ml of ethanol for 6 hours. The disodium salt of the spirobifluorenedicarboxylic acid is precipitated as a yellow solid which is filtered off and heated in 25% strength aqueous HCl to obtain the free acid. The spirobifluorene dicarboxylic acid is recrystallized from glacial acetic acid. This gives 2.2 g (66.6%) of white crystals (m.p. 376° C., IR bands 1685 cm$^{-1}$ C=O).

9,9'-Spirobifluorene-2,2',7,7'-tetracarboxylic acid can be prepared in a similar manner from 2,2',7,7'-tetrabromo-9,9'-spirobifluorene.

f) 9,9'-Spirobifluorene-2,2'-dicarboxylic acid from 9,9'-spirobifluorene via 2,2'-diacetyl-9,9'-spirobifluorene (G. Haas, V. Prelog, Helv. Chim. Acta 52 (1969) 1202; V. Prelog, D. Bedekovic, Helv. Chim. Acta 62 (1979) 2285)

A solution of 3.17 g of 9,9'-spirobifluorene in 30 ml of absolute carbon disulfide is, after addition of 9.0 g of finely powdered, anhydrous $AlCl_3$, admixed dropwise over a period of 10 minutes while stirring with 1.58 g of acetyl chloride in 5 ml of absolute carbon disulfide and is boiled under reflux for 1 hour. The mixture is evaporated to dryness under reduced pressure and is admixed at 0° C. with 100 g of ice and 50 ml of 2N hydrochloric acid. After a conventional workup, the crude product is separated chromatographically over silica gel using benzene/ethyl acetate (10:1). This gives 3.62 g (89%) of 2,2'-diacetyl-9,9'-spirobifluorene (recrystallized from chloroform/ethyl acetate, m.p. from 255° to 257° C.) and 204 mg of 2-acetyl-9,9'-spirobifluorene (recrystallized from chloroform/benzene, m.p. 225° C.). [In addition, the chromatography also enables the 2,2',7-triacetyl-9,9'-spirobifluorene (m.p. from 258° to 260° C.) and 2,2',7,7'-tetraacetyl-9,9'-spirobifluorene (m.p. >300° C.) to be isolated, recrystallized from ethyl acetate/hexane].

2,2',7-Triacetyl- and 2,2',7,7'-tetraacetyl-9,9'-spirobifluorene can be obtained as main product using a different stoichiometry.

First 7.2 g of bromine and then a solution of 3.0 g of 2,2'-diacetyl-9,9'-spirobifluorene in a little dioxane are added dropwise at 0° C. while stirring to a solution of 6.0 g of sodium hydroxide in 30 ml of water. After stirring for a further hour at room temperature, the clear yellow solution is admixed with 1 g of sodium hydrogen sulfite dissolved in 20 ml of water. After acidification with concentrated hydrochloric acid, the precipitated colorless product is filtered off and washed with a little water. Recrystallization with ethanol gives 9,9'-spirobifluorene-2,2'-dicarboxylic acid as clear prisms (m.p. 352° C.).

9,9'-Spirobifluorene-2-carboxylic acid, 9,9'-spirobifluorene-2,2',7-tricarboxylic acid and 9,9'-spirobifluorene-2,2',7,7'-tetracarboxylic acid can be prepared in a similar manner.

g) 2,2'-Bis(bromomethyl)-9,9'-spirobifluorene from 2,2'-dicarboxy-9,9'-spirobifluorene via 9,9'-spirobifluorene-2,2'-dimethanol (V. Prelog, D. Bedekovic, Helv. Chim. Acta 62 (1979) 2285).

At room temperature, 10 g of a 70% strength by weight solution of sodium dihydrobis(2-methoxyethoxy)aluminate (Fluka) in benzene are slowly added dropwise to a suspension of 2.0 g of 2,2'-dicarboxy-9,9'-spirobifluorene (free carboxylic acid) in 20 ml of benzene. After boiling for 2 hours under reflux, during which time the carboxylic acid dissolves, the excess reducing agent is decomposed at 10° C. using water, the mixture is acidified with concentrated hydrochloric acid and is extracted by shaking with chloroform.

After washing with water and drying over magnesium sulfate, the organic phase is evaporated and the residue is recrystallized from benzene. This gives 1.57 g of 9,9'-spirobifluorene-2,2'-dimethanol (m.p. from 254° to 255° C.).

91.5 g of a 33% strength aqueous solution of hydrogen bromide in glacial acetic acid are added dropwise to a solution of 13.5 g of 9,9'-spirobifluorene-2,2'-dimethanol in 400 ml of benzene and the mixture is boiled under reflux for 7 hours. The mixture is then admixed with 200 ml of water and the organic phase is washed with water, dried over magnesium sulfate and evaporated. Chromatography over silica gel using benzene gives 11.7 g of 2,2'-bis(bromomethyl)-9,9'-spirobifluorene as colorless platelets (m.p. from 175° to 177° C.).

h) A solution of 380 mg of 9,9'-spirobifluorene-2,2'-dimethanol in 15 ml of toluene is admixed with 5 g of chromium(VI) oxide on graphite (Seloxcette, Alpha Inorganics) and the mixture is refluxed for 48 hours under nitrogen. It is then filtered with suction through a glass filter and the filtrate is evaporated. Chromatography over silica gel using chloroform and crystallization from methylene chloride/ether gives 152 mg of 9,9'-spirobifluorene-2,2'-dicarbaldehyde (m.p. >300° C.) and 204 mg of 2'-hydroxymethyl1-9,9'-spirobifluorene-2-carbaldehyde (m.p. from 262° to 263° C.)

i) 2,2'-Diamino-9,9'-spirobifluorene

A mixture of 150 ml of concentrated aqueous $HNO_3$ and 150 ml of glacial acetic acid are added dropwise to a boiling solution of 15.1 g of 9,9'-spirobifluorene in 500 ml of glacial acetic acid over a period of 30 minutes and the solution is subsequently refluxed for a further 75 minutes. After cooling and allowing the solution to stand for 1 hour, the same volume of water is added and the product is thereby precipitated. After filtration with suction, 18.5 g of yellow crystals (m.p. from 220° to 224° C.) of 2,2'-dinitro-9,9'-spirobifluorene are obtained. Recrystallization from 250 ml of glacial acetic acid gives 12.7 g of pale yellow crystalline needles (m.p. from 245° to 249° C., analytically pure from 249° to 250° C.).

A mixture of 4.0 ml of dinitrospirobifluorene and 4.0 g of iron powder are heated under reflux in 100 ml of ethanol, while 15 ml of concentrated HCl are added dropwise over a period of 30 minutes. After refluxing for a further 30 minutes, excess iron is filtered off. The green filtrate is added to a solution of 400 ml of water, 15 ml of concentrated $NH_4OH$ and 20 g of sodium potassium tartrate. The white diamine is filtered off from the dark green solution of the iron complex. To purify the diamine, it is dissolved in dilute HCl and stirred at room temperature with activated carbon (Darco) and filtered off. The filtered solution is neutralized dropwise with $NH_4OH$ while stirring (precision glass stirrer) and the precipitated product is filtered off with suction. This gives 3.5 g of white 2,2'-diamino-9,9'-spirobifluorene which can be recrystallized from ethanol (m.p. 243° C.).

j) Synthesis of 2,2',7,7'-tetrabromo-9,9'-spirobifluorene by bromination of solid 9,9'-spirobifluorene using bromine vapor.

3.16 g (10 mmol) of finely powdered 9,9'-spirobifluorene are placed in a flat porcelain evaporating dish ($\phi 2$ about 15 cm). This dish is stood in a desiccator ($\phi$ about 30 cm), on the perforated intermediate plate. On the bottom of the desiccator there are 15.6 g (4.8 ml, 96 mmol) of bromine in a crystallizing dish. The desiccator is closed, but with the ventilation tap opened so that the HBr formed can escape. The desiccator is stood overnight in the fume hood. On the next day, the porcelain dish containing the product, which has been colored orange by bromine, is taken from the desiccator and left to stand in the fume hood for at least a further 4 hours so that excess bromine and HBr can escape.

The product is dissolved in 150 ml of dichloromethane and washed until colorless with 50 ml each of sodium sulfite solution (saturated), sodium hydrogen carbonate solution (saturated) and water. The dichloromethane solution is dried over sodium sulfate and evaporated on a rotary evaporator. The residue is purified by recrystallization from dichloromethane/pentane 4:1. Yield: 5.7 g (92%) of colorless crystals.

$^1$H-NMR ($CDCl_3$, ppm): 6.83 (d, J=1.83 Hz, 4 H, H-1, 1',8,8'); 7.54 (dd, J=7.93, 1.83 Hz, 4 H, H-3,3',6,6'); 7.68 (d, J=7.93 Hz, 4 H, H-4,4',5,5').

k) Synthesis from 2,2',4,4',7,7'-hexabromo-9,9'-spirobifluorene 200 mg of anhydrous FeCl$_3$ are added to a solution of 3.16 g (10 mmol) of 9,9'-spirobifluorene in 20 ml of methylene chloride and the mixture is treated with ultrasound. The reaction flask is protected from light by means of aluminum foil. Subsequently, at the boiling point, 9.85 g (3.15 ml, 62 mmol) of bromine in 5 ml of methylene chloride are added dropwise over a period of 15 minutes. The solution is boiled under reflux and treated with ultrasound for a further 20 hours. After cooling, petroleum ether is added and the mixture is filtered with suction. The product is further purified by recrystallization from THF/methanol and drying for 5 hours at 80° C. Yield: 6.15 g (77%) of colorless crystals.

$^1$H-NMR (CDCl$_3$, ppm): 6.76 (d, J=1.53 Hz, 2H, H 1,1'); 6.84 (d, J=1.83 Hz, 2H, H-8,8'); 7.60 (dd, J=8.54, 1.83 Hz, 2 H, H-6,6'); 7.75 (d, J=1.53 Hz, 2 H, H-3,3'); 8.49 (d, J=8.54 Hz, 2 H, H-5,5').

l) Synthesis of 2,7-dibromo-9,9'-spirobifluorene

The Grignard reagent prepared from 0.72 g (30 mmol) of magnesium turnings and 5.1 ml (30 mmol) of 2-bromobiphenyl in 15 ml of diethyl ether is added dropwise over a period of 2 hours, while stirring (in an ultrasonic bath), to a boiling suspension of 10.0 g (29.6 mmol) of 2,7-dibromo-9-fluorenone in 100 ml of dry diethyl ether. After the addition is complete, the mixture is boiled for a further 3 hours. After cooling overnight, the precipitated solid is filtered off with suction and washed with cold ether. The magnesium complex filtered off is hydrolyzed in a solution of 15 g of ammonium chloride in 250 ml of ice water. After 1 hour, the 9-(2-biphenylyl)-2,7-dibromo-9-fluorenol formed is filtered off with suction, washed with water and sucked dry. For the ring-closure reaction, the dried fluorenol is boiled in 100 ml of glacial acetic acid for 6 hours, after addition of 3 drops of concentrated HCl. The mixture is allowed to crystallize overnight, the product formed is filtered off with suction and is washed with glacial acetic acid and water.

Yield: 11 g (77%) of 2,7-dibromo-9,9'-spirobifluorene. It can be further purified by recrystallization from THF.

$^1$H-NMR (CDCl$_3$, ppm): 6.73 (d, J=7.63 Hz, 2 H, H-1',8'); 6.84 (d, J=1.83 Hz, 2 H, H-1,8); 7.15 (td, J=7.63, 1.22 Hz, 2 H, H-2',7'); 7.41 (td, J=7.63, 1.22 Hz, 2H, H-3',6'); 7.48 (dd, J=8.24, 1.83 Hz, 2 H, H-3,6); 7.67 (d, J=8.24; 2 H; H-4,5); 7.85 (d, J=7.63, 2H, H-4',5').

m) Synthesis of 2,7-dicarbethoxy-9,9'-spirobifluorene

The Grignard reagent prepared from 0.97 g (40 mmol) of magnesium turnings and 9.32 g (6.8 ml, 40 mmol) of 2-bromobiphenyl in 50 ml of dry diethyl ether is added dropwise over a period of 2 hours to a boiling solution of 13 g (40 mmol) of 2,7-dicarbethoxy-9-fluorenone in 100 ml of dry diethyl ether. After the addition is complete, the mixture is boiled for a further 3 hours. After cooling overnight, the precipitated solid is filtered off with suction and washed with cold ether. The magnesium complex filtered off with suction is hydrolyzed in a solution of 15 g of ammonium chloride in 250 ml of ice water. After 1 hour, the 9-(2-biphenylyl)-2,7-dicarbethoxy-9-fluorenol formed is filtered off with suction, washed with water and sucked dry. For the ring-closure reaction, the dried fluorenol is boiled in 100 ml of glacial acetic acid for 6 hours, after addition of 3 drops of concentrated HCl. The mixture is allowed to crystallize overnight, the product formed is filtered off with suction and washed with glacial acetic acid and water.

Yield: 15.1 g (82%) of 2,7-dicarbethoxy-9,9'-spirobifluorene. It can be further purified by recrystallization from ethanol.

$^1$H-NMR (CDCl$_3$, ppm): 1.30 (t, J=7.12 Hz, 6 H, ester-CH$_3$); 4.27 (q, J=7.12 Hz, 4 H, ester-CH$_2$); 6.68 (d, J=7.63 Hz, 2 H, H-1',8'); 7.11 (td, J=7.48, 1.22 Hz, 2H, H-2',7'); 7.40 (td, J=7.48, 1.22 Hz, 4 H, H-1,8,3',6'); 7.89 (dt, J=7.63, 0.92 Hz, 2 H, H-4',5'); 7.94 (dd, J=7.93, 0.6 Hz, 2 H, H-4,5); 8.12 (dd, J=7.93, 1.53 Hz, 2 H, H-3,6)

n) Synthesis of 2,7-dibromo-2',7'-diiodo-9,9'-spirobifluorene

In a 250 ml of three-necked flask fitted with reflux condenser and dropping funnel, a suspension of 2.37 g of 2,7-dibromo-9,9'-spirobifluorene in 50 ml of glacial acetic acid is admixed at 80° C. with 5 ml of water and, after addition of 2 ml of concentrated sulfuric acid, 1.27 g of iodine, 0.53 g of iodic acid and 5 ml of carbon tetrachloride, is stirred until the iodine color disappears. The solid is subsequently filtered off with suction and washed well with water. After drying, the precipitate is dissolved in 150 ml of dichloromethane and washed successively with Na$_2$SO$_3$ solution, NaHCO$_3$ solution and water. The dichloromethane phase is dried over Na$_2$SO$_4$ and subsequently evaporated. This gives colorless crystals of 2,7-dibromo-2',7'-diiodo-9,9'-spirobifluorene in quantitative yield. It can be further purified by recrystallization from dichloromethane/pentane.

$^1$H-NMR (CHCl$_3$, ppm): 6.80 (d, J=1.83 Hz, 2 H), 6.99 (d, J=1.53 Hz, 2 H), 7.51 (dd, J=8.24, 1.83 Hz, 2 H), 7.54 (d, J=7.93 Hz, 2 H), 7.65 (d, J=8.24 Hz, 2 H), 7.72 (dd, J=8.24, 1.53 Hz, 2 H).

B. Synthesis examples

Example 1

2,2'-Bis(benzofuran-2-yl)-9,9'-spirobifluorene (using a method similar to that of W. Sahm, E. Schinzel, P. Jürges, Liebigs Ann. Chem. (1974) 523)

2.7 g (22 mmol) of salicylaldehyde and 5.0 g (10 mmol) of 2,2'-bis(bromomethyl)-9,9'-spirobifluorene are dissolved at room temperature in 15 ml of DMF and admixed with 0.9 g (22.5 mmol) of pulverized NaOH and a spatula tip of KI. The mixture is heated to boiling and stirred for 1 hour at the boiling point. After cooling, the reaction solution is admixed with a mixture of 0.5 ml of concentrated hydrochloric acid, 7 ml of water and 7 ml of methanol. The mixture is stirred for a further 1 hour at room temperature, the crystalline reaction products are filtered off with suction, washed first with cold methanol, then with water and dried in vacuo atL 60° C. This gives 4.6 g (79%) 2,2

5.85 g (10 mmol) 2,2'-bis(2-formylphenyloxymethyl)9,9'-spirobifluorene are mixed in 10 ml of toluene with 2.1 g (22.5 mmol) of freshly distilled aniline. A spatula tip of p-toluenesulfonic acid is added and the mixture is heated at the boiling point on a water separator until no more water is separated off (from about 3 to 5 hours). On cooling the reaction mixture, the corresponding bis-benzylidenephenylamine precipitates in crystalline form. It is filtered off with suction, washed with methanol and dried in vacuo at 60° C. It can be further purified by recrystallization from DMF.

7.35 g (10 mmol) of the bis-benzylidenephenylamine and 0.62 g (11 mmol) of KOH are introduced under nitrogen into 30 ml of DMF. The mixture is subsequently heated at 100° C. for 4 hours while stirring. After cooling to room temperature, the precipitate is filtered off with suction and washed with a little DMF and water. After drying at 60° C. in a vacuum drying oven, the 2,2'-bis(benzofuran-2-yl)-9,9'-spirobifluorene can be purified by recrystallization from methyl benzoate.

Example 2

2,2',7,7'-Tetra(benzofuran-2-yl)-9,9'-spirobifluorene can be prepared by a similar method to Example 1 using an appropriately altered stoichiometry.

Example 3
2,2',7,7'-Tetraphenyl-9,9'-spirobifluorene 5 g (7.9 mmol) of 2,2',7,7'-tetrabromo-9,9-spirobifluorene, 3.86 g (31.6 mmol) of phenylboronic acid, 331.5 mg (1.264 mmol) of triphenylphosphine and 70.9 mg (0.316 mmol) of palladium acetate are slurried in a mixture of 65 ml of toluene and 40 ml of aqueous sodium carbonate solution (2M). With vigorous stirring, the mixture is boiled under reflux for 24 hours. After cooling to room temperature, the solid is filtered off with suction, washed with water and dried in vacuo at 50° C. 2.58 g are obtained. The filtrate is extracted with 50 ml of toluene and the dried organic phase is evaporated to dryness. This gives a further 1.67 g. Total yield: 4.25 g (86%)

Example 4
2,2',7,7'-Tetrakis(biphenyl)-9,9'-spirobifluorene 5 g (7.9 mmol) of 2,2',7,7'-tetrabromospirobifluorene, 6.57 g (33.2 mmol) of biphenylboronic acid, 331.5 mg (1.264 mmol) of triphenylphosphine and 70.9 mg (0.316 mmol) of palladium acetate are slurried in a mixture of 65 ml of toluene and 40 ml of aqueous sodium carbonate solution (2M). With vigorous stirring, the mixture is boiled under reflux for 24 hours. After cooling to room temperature, the solid is filtered off with suction, washed with water and dried in vacuo at 50° C.

Yield: 5.95 g (81%)

Example 5
Synthesis of 2,2',7,7'-tetrabiphenylyl-9,9'-spirobifluorene

In a 250 ml two-necked flask fitted with reflux condenser and precision glass stirrer, 5.5 g of tetrabromospirobifluorene, 7.2 g of biphenylboronic acid and 400 mg of tetrakis(triphenylphosphine)palladium are slurried in a mixture of 100 ml of toluene and 50 ml of potassium carbonate solution. The mixture is boiled under reflux for 8 hours under a blanket of inert gas while stirring with a precision glass stirrer. After cooling, the product is filtered off with suction, the precipitate is washed with water and dried. The toluene phase is separated off from the filtrate and the aqueous phase is extracted once by shaking with chloroform. The combined organic phases are dried over sodium sulfate and evaporated on a rotary evaporator, thus giving a second fraction of the product. The two product fractions are combined (8 g) and dissolved in chloroform. The chloroform solution is boiled with activated carbon and filtered through a short column of silica gel. After evaporation on a rotary evaporator and recrystallization from chloroform/pentane, colorless crystals which fluoresce blue under UV illumination are obtained. Melting point: 408° C. (DSC).

$^1$H-NMR (CDCl$_3$, ppm): 7.14 (d, J=1.53 Hz, 4 H); 7.75 (dd, J=7.93, 1.53 Hz, 4 H); 8.01 (d, J=7.93 Hz, 4 H); 7.34 (dd, J=7.32, 1.37 Hz, 4 H); 7.42 (t, J=7.32 Hz, 8 H); 7.58 (24 H).

Example 6
Synthesis of 2,2',4,4',7,7'-hexabiphenylyl-9,9'-spirobifluorene

In a 250 ml two-necked flask fitted with reflux condenser and precision glass stirrer, 1.6 g of hexabromospirobifluorene and 3 g of biphenylboronic acid are slurried in a mixture of 50 ml of toluene and 50 ml of 1M potassium carbonate solution. The mixture is refluxed under nitrogen and 115 mg of tetrakis(triphenylphosphine)palladium in 5 ml of toluene are added. The mixture is boiled under reflux for 7 hours while stirring. After the reaction is complete, the cooled solution is filtered and the filtrate is extracted twice by shaking with water (to improve the phase separation, chloroform is added). The organic phase is dried over sodium sulfate, filtered through a short column of silica gel and subsequently evaporated on a rotary evaporator. The product is further purified by recrystallization from dichloromethane/pentane. This gives 2 g (80%) of colorless crystals which fluoresce blue under UV illumination.

$^{13}$C-NMR [360 MHz; ATP, broad-band decoupled] (CDCl$_3$, ppm): 65.94 (1C, spiro-C); 126.95 (6C, CH), 126.97 (6C, CH), 127.17 (6C, CH), 127.35 (6C, CH), 127.36 (6C, CH), 127.39 6C, CH), 127.52 (6C, CH), 128.73 (6C, CH), 128.75 (6C, CH), 128.94 (6C, CH), 129.90 (4 C, CH), 137.77 (2 C), 137.86 (2 C), 139.43 (2 C), 139.69 (2 C), 139.89 (2 C), 140.09 (2 C), 140.17 (2 C), 140.22 (2 C), 140.30 (2 C), 140.63 (2 C), 140.64 (2 C), 140.68 (2 C), 140.72 (2C), 140.74 (2 C), 150.45 (2C), 150.92 (2C).

Example 7
Synthesis of 2,2'-bis[5-(p-t-butylphenyl)-1,3,4-oxadiazol-2-yl]-9,9'-spirobifluorene from 9,9'-spirobifluorene-2,2'-dicarboxylic acid chloride and 5(4-t-butylphenyl)tetrazole a) Synthesis of 5-(4-t-butylphenyl)tetrazole In a 250 ml round-bottomed flask fitted with reflux condenser, 4.9 g of p-t-butylbenzonitrile, 3.82 g of lithium chloride and 5.85 g of sodium azide and 8.2 g of triethylammonium bromide in 100 ml of DMF are heated at 120° C. for 8 hours. After cooling to room temperature, 100 ml of water are added and the mixture is admixed in an ice bath with dilute hydrochloric acid until no further solid precipitates. The precipitate is filtered off with suction, washed with water and dried. Recrystallization from ethanol/water gives 4.4 g of colorless crystals.

b) 9,9'-Spirobifluorene-2,2'-dicarboxylicacidchloride

In a 100 ml flask fitted with reflux condenser and drying tube, 2 g (5 mmol) of 9,9'-spirobifluorene-2,2'-dicarboxylic acid together with 20 ml of freshly distilled thionyl chloride and 3 drops of DMF are boiled under reflux for 4 hours. After cooling, the reflux condenser is replaced by a distillation bridge and excess thionyl chloride is distilled off in vacuo, 40 ml of petroleum ether (30°–60° C.) are added to the residue and are distilled off, leaving the crystalline acid chloride.

c) 2,2'-Bis[5-(p-t-butylphenyl)-1,3,4-oxadiazol-2-yl]-9,9'-spirobifluorene 2.0 g (11 mmol) of 5-(4-t-butylphenyl)tetrazole dissolved in 20 ml of anhydrous pyridine are added to the acid chloride and the mixture is refluxed under inert gas for 2 hours. After cooling, the mixture is added into 200 ml of water and allowed to stand for 2 hours. The precipitated oxadiazole derivative is filtered off with suction, washed with water and dried in vacuo. It is subsequently chromatographed over silica gel using chloroform/ethyl acetate (99:1) and recrystallized from chloroform/pentane. This gives 2.4 g of colorless crystals.

$^1$H-NMR (CDCl$_3$), ppm): 1.31 (s, 18 H, t-butyl), 6.77 (d, J=7.32 Hz, 2 H), 7.18 (td, J=7.48, 1.22 Hz, 2 H), 7.44 (td, J=7.40, 1.22 Hz, 2 H), 7.46 (d, J=8.54 Hz, 4 H), 7.50 (d, J=1.22 Hz, 2 H), 7.94 (d, J=8.54 Hz, 4 H), 8.02 (d, J=7.93 Hz, 6 H), 8.20 (dd, J=7.93, 1.53 Hz, 2 H).

C. Use example 2,2',7,7'-Tetrakis(biphenyl)-9,9'-spirobifluorene is dissolved in chloroform (30 mg/ml) and applied by means of spincoating (1000 rpm) to a glass support coated with indium/tin oxide (ITO), with a homogeneous transparent film being formed. An electrode of Mg/Ag (80/20) is applied to this film by vapor deposition in vacuo. On application of an electric potential between the ITO electrode and the metal electrode, with the metal electrode having a negative potential relative to the ITO electrode, a blue electroluminescence is observed.

We claim:

1. An electroluminescence device including an active layer comprising a spirobifluorene compound of formula (II)

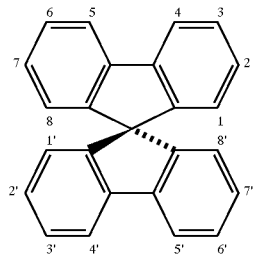

where the benzo groups can be substituted and/or fused independently of one another.

2. An electroluminescence device including an active layer comprising a spirobifluorene compound of the formula (III),

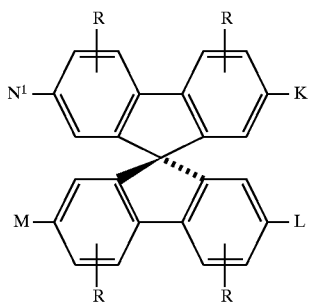

where the symbols and indices have the following meanings:

K, L, M, N¹ are identical or different and are

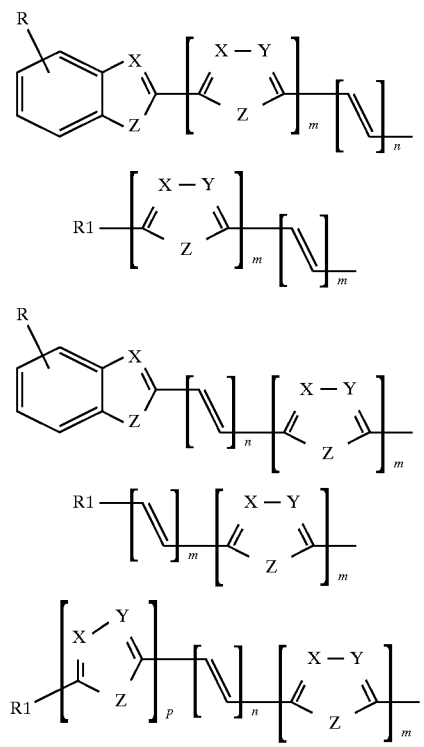

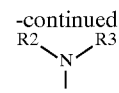

R can be identical or different on each appearance and have the same meanings as K, L, M, N or is H, a linear or branched alkyl, alkoxy or ester group having from 1 to 22 carbon atoms, —CN, —NO$_2$, —NR$^2$R$^3$, —Ar or —O—Ar;

Ar is phenyl, biphenyl, 1-naphthyl, 2-naphthyl, 2-thienyl, 2-furyl, with each of these groups being able to bear one or two radicals R, m, n, p are 0, 1, 2 or 3;

X, Y are identical or different and are CR or nitrogen;

Z is —O—, —S—, —NR$^1$—, —CR$^1$R$^4$—, —CH=CH—, —CH=N—;

R$^1$, R$^4$ can be identical or different and have the same meanings as R;

R$^2$, R$^3$ are identical or different and are H, a linear or branched alkyl group having from 1 to 22 carbon atoms, —Ar, or 3-methylphenyl.

3. An electroluminescence device including an active layer comprising a spirobifluorene compound selected from the group consisting of the spirobifluorene compounds of the formula (IIIa) to (IIIg), wherein formula III is:

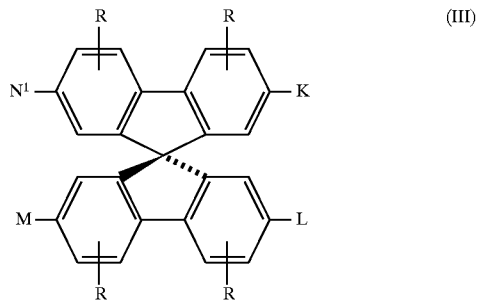

and the spirobifluorene compounds (IIIa to IIIg) are derivatives of formula (III) as follows:

IIIa) K=L=M=N¹ and is selected from the group consisting of:

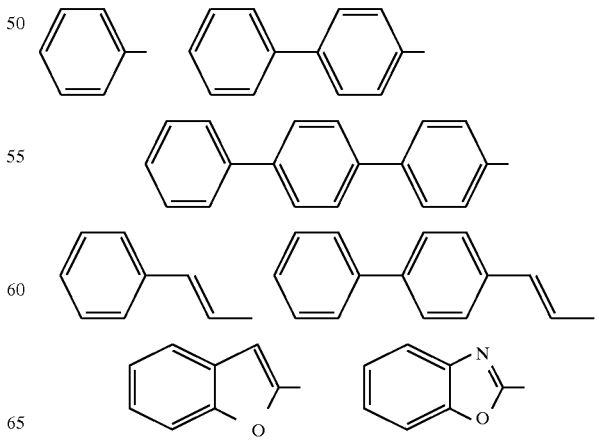

-continued
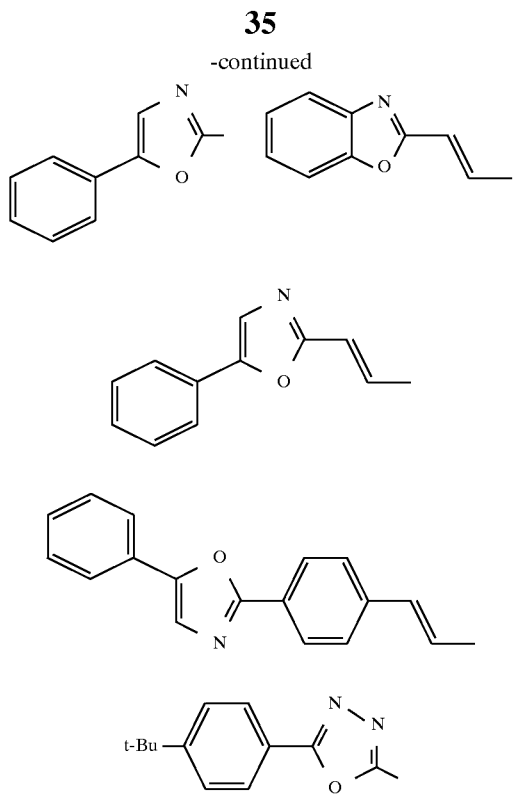
R=C$_1$–C$_{22}$-alkyl, C$_2$H$_4$SO$_3$—
IIIb) K=M=H and N$^1$=L and is selected from the group consisting of:
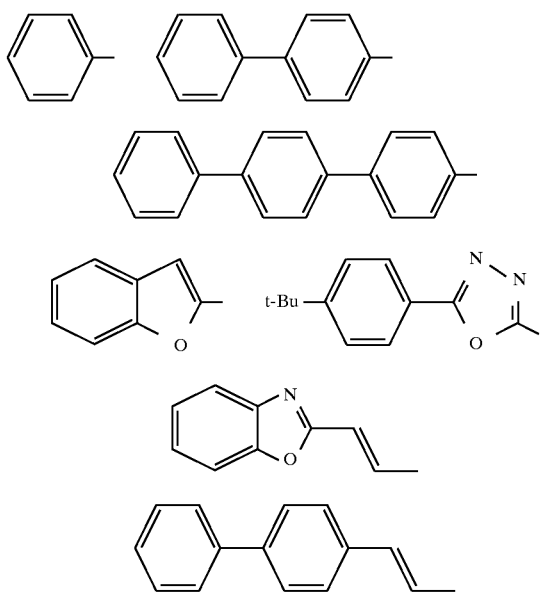
-continued
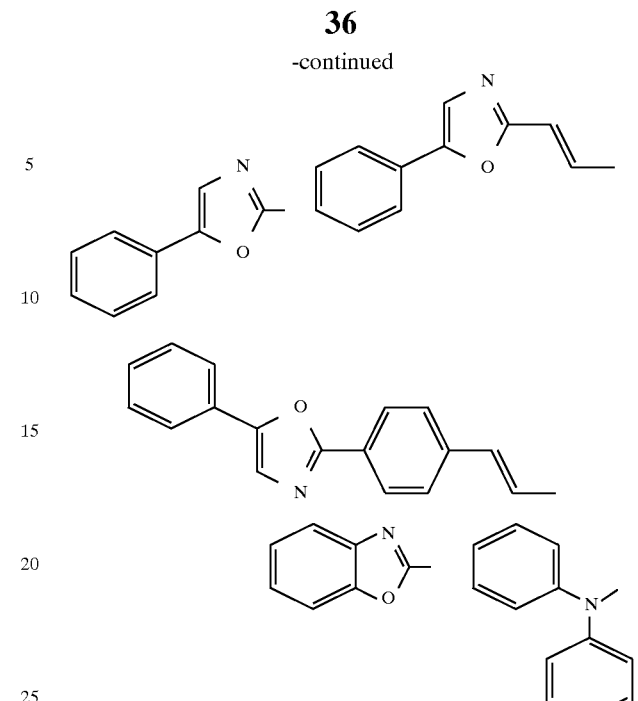
IIIc) K=M and is selected from the group consisting of:
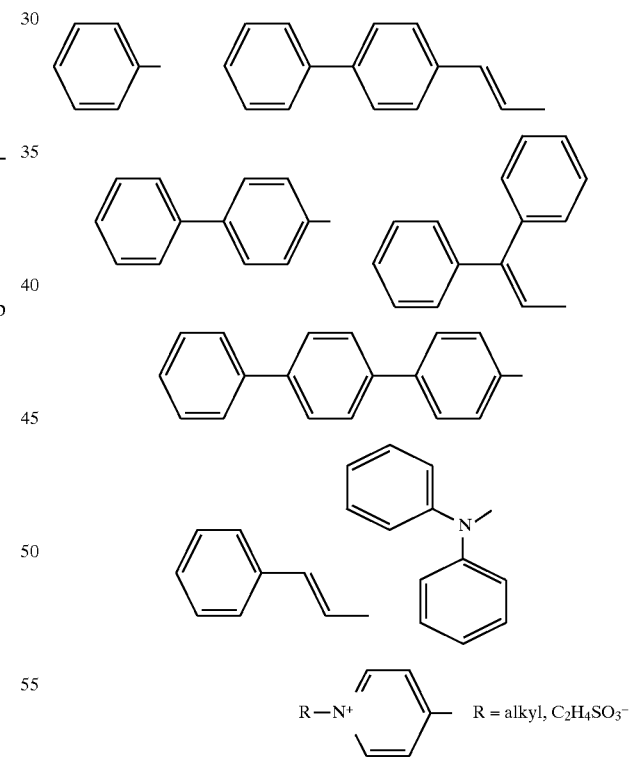
R = alkyl, C$_2$H$_4$SO$_3^-$
and N$^1$=L and is selected from the group consisting of:
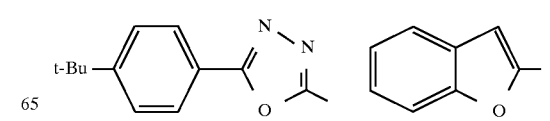

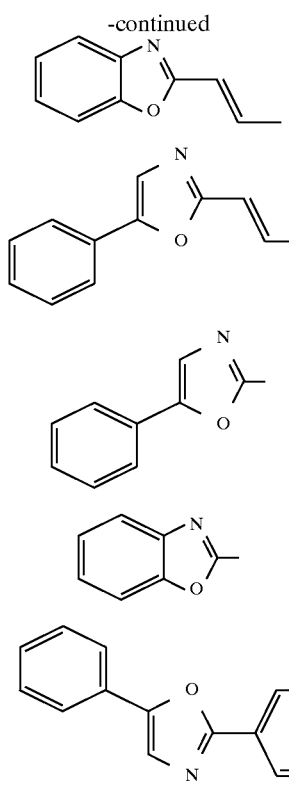
IIId) K=M and is selected from the group consisting of:
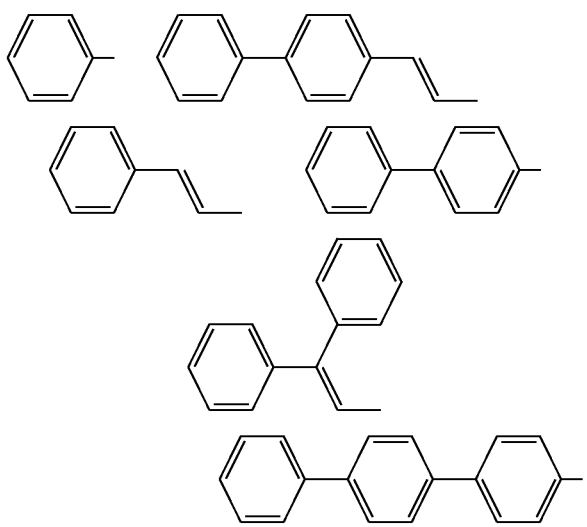
and N¹=L and is selected from the group consisting of:
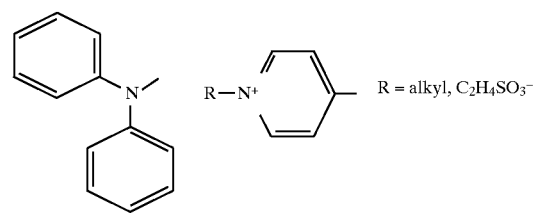
IIIe) K=L=H and M=N¹ and is selected from the group consisting of:
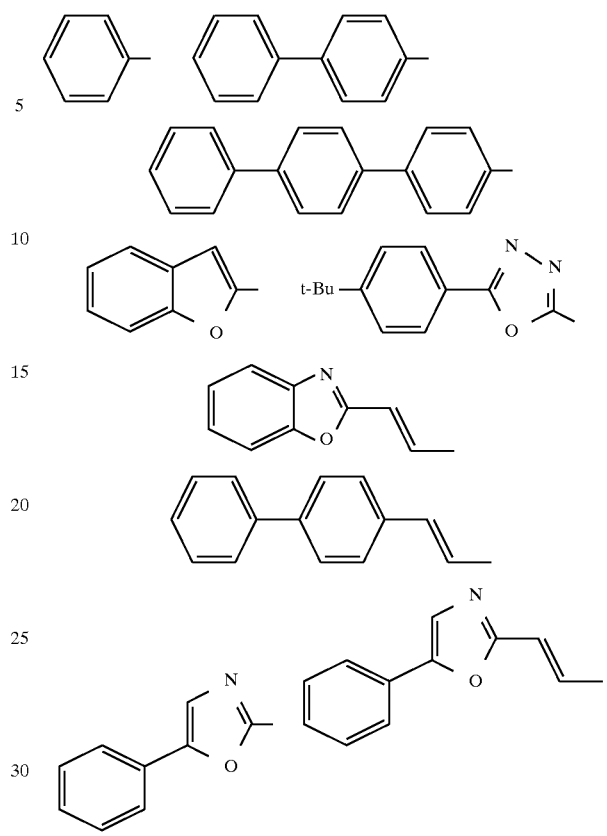
IIIf) K=L and is selected from the group consisting of:

39
-continued
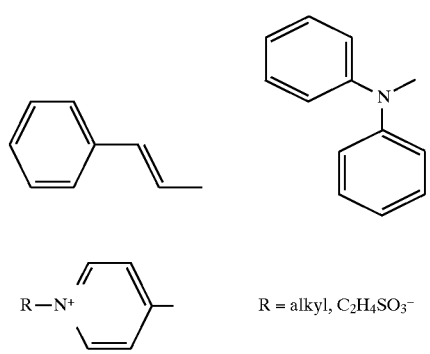
and M=N¹ and is selected from the group consisting of:
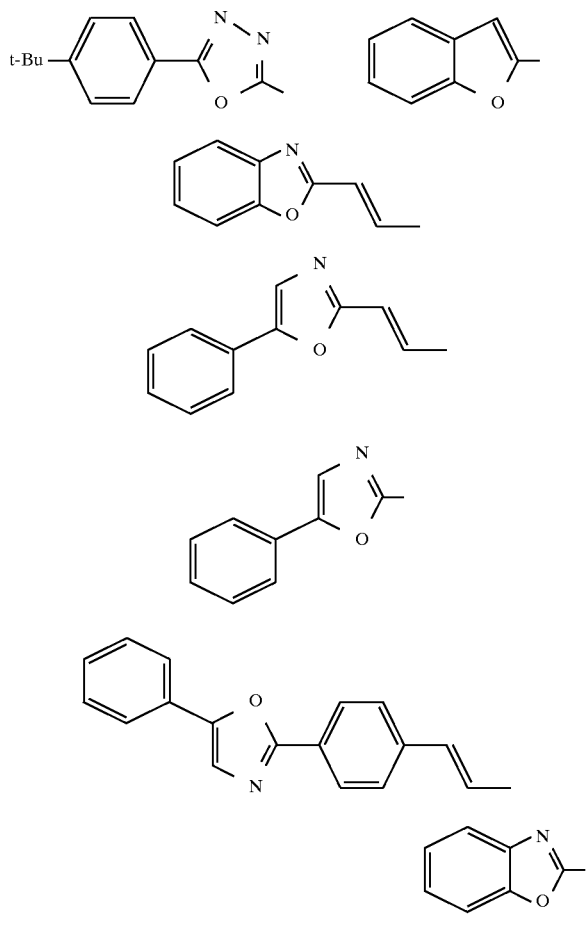
IIIg) K=L and is selected from the group consisting of:
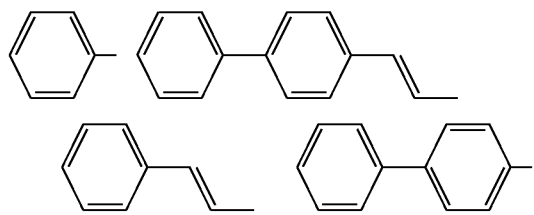
40
-continued
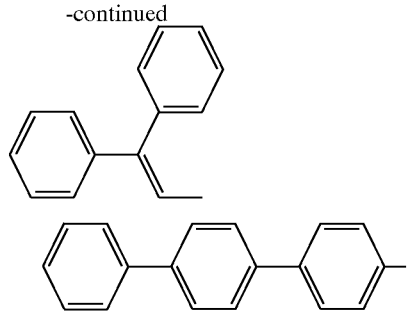
and M=N¹ and is selected from the group consisting of:
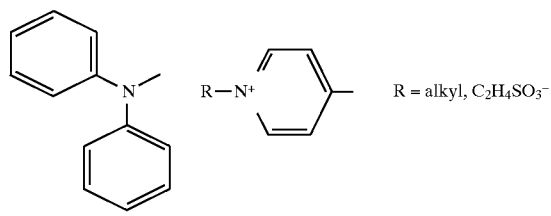
4. A spiro compound of the formula (V)
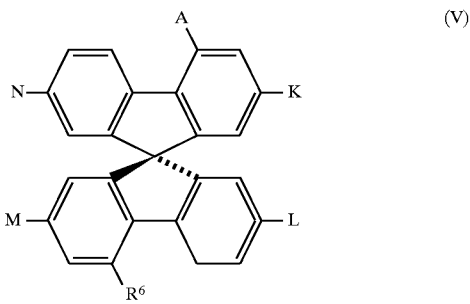
(V)
where the symbols have the following meanings:
A, B, K, L, M, N¹ are identical or different and are each
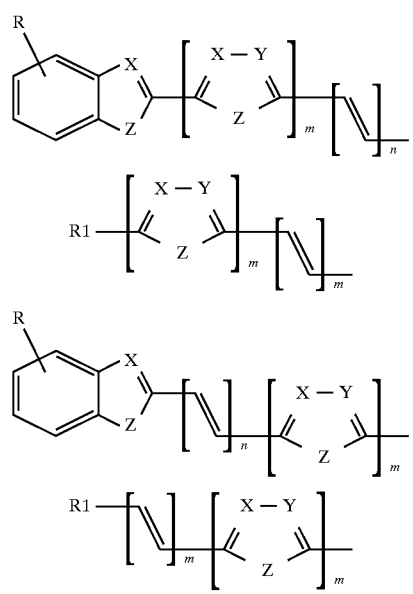

-continued

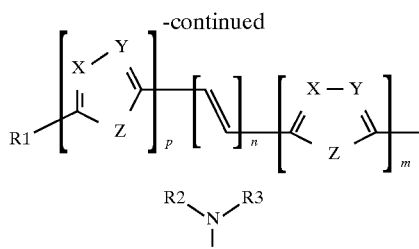

and A, B can also be identical or different and each be a linear or branched alkyl, alkyloxy or ester group having from 1 to 22 carbon atoms, —CN, —NO$_2$, —Ar or —O—Ar;

R is H, a linear or branched alkyl, alkoxy or ester group having from 1 to 22 carbon atoms, —CN, —NO$_2$, —NR$^2$R$^3$, —Ar or —O—Ar;

Ar is phenyl, biphenyl, 1-naphthyl, 2-naphthyl, 2-thienyl, 2-furanyl, with each of these groups being able to bear one or two radicals R, m, n, p are 0, 1, 2 or 3;

X, Y are identical or different and are CR or nitrogen;

Z is —O—, —S—, —NR$^1$—, —CR$^1$R$^4$—, —CH=CH—, —CH=N—;

R$^1$, R$^4$ can be identical or different and have the same meanings as R;

R$^2$, R$^3$ are identical or different and are H, a linear or branched alkyl group having from 1 to 22 carbon atoms, —Ar or 3-methylphenyl.

5. The active layer as claimed in claim 1, wherein the spiro compound is a light-emitting material.

6. The active layer as claimed in claim 1, wherein the spiro compound is a charge-transport material.

7. The active layer as claimed in claim 1, wherein the spiro compound is a charge-injection material.

8. An electroluminescence device comprising an active layer which comprises one or more compounds of the formula (II) as claimed in claim 1.

9. The electroluminescence device as claimed in claim 8, wherein the active layer is a light-emitting layer.

10. The electroluminescence device as claimed in claim 8, wherein the active layer is a charge-transport layer.

11. The electroluminescence device as claimed in claim 8, wherein the active layer is a charge-injection layer.

12. An electroluminescence device comprising an active layer which comprises one or more compounds of the formula (II) as claimed in claim 1.

* * * * *